United States Patent [19]

Reitz et al.

[11] Patent Number: 5,344,991
[45] Date of Patent: Sep. 6, 1994

[54] 1,2 DIARYLCYCLOPENTENYL COMPOUNDS FOR THE TREATMENT OF INFLAMMATION

[75] Inventors: David B. Reitz; Jinglin Li, both of Chesterfield, Mo.

[73] Assignee: G.D. Searle & Co., Chicago, Ill.

[21] Appl. No.: 146,359

[22] Filed: Oct. 29, 1993

[51] Int. Cl.$^5$ .................. C07C 317/14; C07C 311/15; A61K 31/10; A61K 31/18
[52] U.S. Cl. ...................... 568/34; 558/413; 562/429; 564/84
[58] Field of Search .................. 564/84; 514/602, 709, 514/520, 570; 568/34; 558/413; 562/429

[56] References Cited

U.S. PATENT DOCUMENTS

| | | | |
|---|---|---|---|
| 3,957,795 | 5/1976 | Kubela et al. | 260/293.65 |
| 4,206,220 | 6/1980 | Sloan | 424/274 |
| 4,229,207 | 10/1980 | Laanio et al. | 71/107 |
| 4,393,079 | 7/1983 | Cole et al. | 424/331 |
| 4,543,207 | 9/1985 | Sato et al. | 252/570 |

OTHER PUBLICATIONS

E. J. Corey et al., *J. Amer. Chem. Soc.*, 85, 1788–1792, (1963).
D. Y. Curtin et al., *J. Org. Chem.*, 36, 565–72, (1971).
O. P. Malik et al., *Ind. J. Chem.*, 14B, 975–78, (1976).
Somers et al., *J. Photochem. Photobio.*, 48A, 353–74, (1989).
W. H. Laarhoven, *Pure & Appl. Chem.*, 56, 1225–40, (1984).
H. Ohashi et al., *Phytochemistry*, 31, 1371–1373, (1992).

*Primary Examiner*—José G. Dees
*Assistant Examiner*—Barbara S. Frazier
*Attorney, Agent, or Firm*—Joseph W. Bulock

[57] ABSTRACT

A class of 1,2-diarylcyclopentenyl compounds is described for use in treating inflammation and inflammation-related disorders. Compounds of particular interest are defined by Formula I:

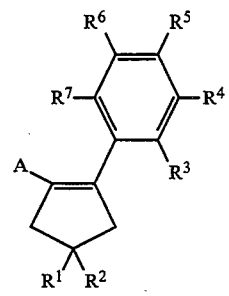

wherein A is selected from

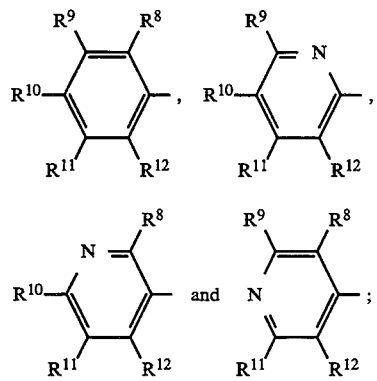

each of $R^1$ and $R^2$ is independently selected from hydrido, methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; and wherein each of $R^5$ and $R^{10}$ is independently selected from hydrido, fluoro, chloro, bromo, iodo, methyl, ethyl, methoxy, methylthio, cyano, trifluoromethyl, hydroxymethyl, methoxymethyl, methylsulfonyl and sulfamyl; provided that when A is (Abstract continued on next page.)

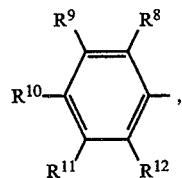
$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.
31 Claims, No Drawings

1,2 DIARYLCYCLOPENTENYL COMPOUNDS FOR THE TREATMENT OF INFLAMMATION

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including increased gastric acid levels and life threatening ulcers, that limit their therapeutic potential. A popular current alternative to NSAIDs is the use of corticosteroids, which have even more drastic side effects, especially when long term therapy is involved.

1,2-Diarylcycloalkenes have been made and used for a variety of utilities. For example, U.S. Pat. No. 4,543,207 to Sato, et al., describes diphenyl cyclohexene as an electrical insulating oil additive. U.S. Pat. No. 4,229,207, to Laanio, et al., describes 1,2-diphenylcyclohex-1-ene-4-carboxylic acid esters, specifically, 1,2-di(4-phenylsulfonic acid)-cyclohex-1-ene-4-carboxylic acid ethyl ester. These ester compounds are reported to be effective as plant growth regulating agents and as post-emergent herbicides for controlling wild oats.

The synthesis of 3,4-diphenyl-$\Delta^3$-cyclopentenone ethylene ketal is described as an intermediate for forming carbinols [E. J. Corey, et al., *J. Amer. Chem., Soc.,* 85, 1788–1792 (1963)]. 2,3-Bis-(4-hydroxyphenyl)-2-cyclopenten-1-one has been identified from the knot resin powder of Arqaucaria angustifolia [H. Ohash, et al., *Phytochemistry*, 31, 1371–73 (1992)].

Substituted 1,2 -diphenylcyclopentenes have been synthesized for use in studies of their rotational behavior, includes specifically, 1-(2,4-Dimethylphenyl)-2-phenylcyclopentene [D. Y. Curtin, et al., *J. Org. Chem.*, 36, 565–72 (1971)]. 1,2-Di-(2'-methoxyphenyl)-$\Delta^1$-cyclopentene has been identified as an impurity in the synthesis of cannabinoids [O. P. Malik, et al., *Ind. J. Chem.*, 14B, 975–78 (1976)].

1-(Substitutedphenyl)-2-phenylcyclopentenes have been synthesized to study their photochemical reactions into phenanthrene derivatives. Compounds with meta substituents, such as 1-(3-chlorophenyl)-2-phenylcyclopentene, are described in Somers, et al., *J. Photochem. Photobiol.*, 48A, 353–74 (1989). Para substituents, including specifically 1-(4-fluorophenyl)-2-phenylcyclopentene, are described in Laarhoven, *Pure & Appl. Chem.*, 56, 1225–40 (1984).

DESCRIPTION OF THE INVENTION

A class of 1,2-diarylcyclopentene compounds useful in treating inflammation-related disorders is defined by Formula I:

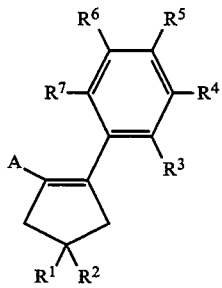

wherein A is selected from

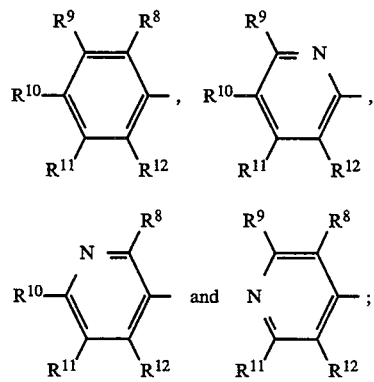

wherein each of $R^1$ and $R^2$ is independently selected from alkyl, hydrido, hydroxyalkyl, halo, haloalkyl, alkylcarboxyl and carboxyl; and where if each of $R^3$ through $R^{12}$ is independently selected from hydrido, halo, alkyl, alkylthio, cyano, haloalkyl, alkoxy, hydroxyalkyl, alkoxyalkyl, alkylsulfonyl and sulfamyl; provided that when A is

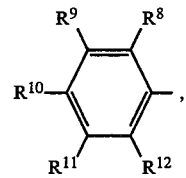

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

The phrase "further provided", as used in the above description, is intended to mean that the denoted proviso is not to be considered conjunctive with the other provisos.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erythematosus, osteoarthritis and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as anti-inflammatory agents, such as for the treatment of arthritis, with the additional benefit of having significantly less harmful side effects.

A preferred class of compounds consists of those compounds of Formula I wherein each of $R^1$ and $R^2$ is independently selected from alkyl, hydrido, hydroxyalkyl, halo, haloalkyl, alkylcarboxyl and carboxyl; wherein each of $R^3$, $R^4$, $R^6$ through $R^9$, $R^{11}$ and $R^{12}$ is independently selected from hydrido, alkyl and halo; and wherein each of $R^5$ and $R^{10}$ is independently selected from hydrido, halo, alkyl, alkylthio, cyano, haloalkyl, alkoxy, hydroxyalkyl, sulfamyl, alkoxyalkyl and alkylsulfonyl; provided that when A is

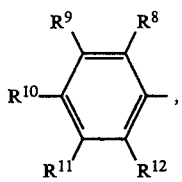

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

A class of compounds of particular interest consists of those compounds of Formula I wherein each of $R^1$ and $R^2$ is independently selected from hydrido, methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; and wherein each of $R^5$ and $R^{10}$ is independently selected from hydrido, fluoro, chloro, bromo, iodo, methyl, ethyl, methoxy, methylthio, cyano, trifluoromethyl, hydroxymethyl, methoxymethyl, methylsulfonyl and sulfamyl; provided that when A is

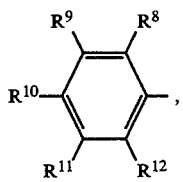

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and method; and further provided that $R^5$ and $R^{10}$ are not both method; or a pharmaceutically suitable salt thereof.

A class of compounds of more particular interest consists of those compounds of Formula I wherein each of $R^1$ and $R^2$ is independently selected from methyl, hydrido, fluoro and carboxyl; wherein each of $R^3$, $R^4$, $R^6$ through $R^9$, $R^{11}$ and $R^{12}$ are selected from hydrido, methyl, fluoro and chloro; and wherein each of $R^5$ and $R^{10}$ is independently selected from hydrido, fluoro, chloro, methyl, methylthio, cyano, trifluoromethyl, hydroxymethyl, methoxymethyl, methylsulfonyl and sulfamyl; provided that when A is

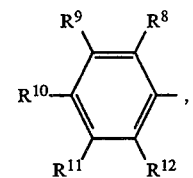

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

Within Formula I there is a subclass of compounds of high interest represented by Formula II:

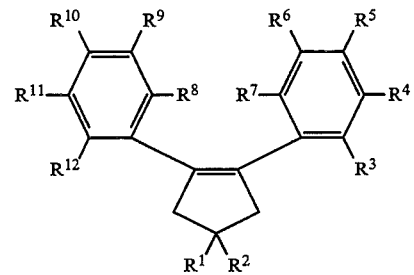

wherein each of $R^1$ and $R^2$ is independently selected from alkyl, hydrido, hydroxyalkyl, halo, haloalkyl, alkylcarboxyl and carboxyl; and wherein each of $R^3$ through $R^{12}$ is independently selected from hydrido, halo, alkyl, alkylthio, cyano, haloalkyl, alkoxy, hydroxyalkyl, alkoxyalkyl, alkylsulfonyl and sulfamyl; provided that $R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

A preferred class of compounds consists of those compounds of Formula II wherein $R^1$ and $R^2$ are identical radicals selected from alkyl, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein each of $R^3$, $R^4$, $R^6$ through $R^9$, $R^{11}$ and $R^{12}$ is independently selected from hydrido, alkyl and halo; wherein $R^5$ is alkylsulfonyl or sulfamyl; and wherein $R^{10}$ is selected from hydrido, halo, alkyl, alkylthio, cyano, haloalkyl, alkoxy, hydroxyalkyl and alkoxyalkyl; or a pharmaceutically-acceptable salt thereof.

A class of compounds of particular interest consists of those compounds of Formula II wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; wherein $R^5$ is methylsulfonyl or sulfamyl; and wherein $R^{10}$ is selected from hydrido, fluoro, chloro, bromo, iodo, methyl, ethyl, methoxy, methylthio, cyano, trifluoromethyl, hydroxymethyl and methoxymethyl; or a pharmaceutically-acceptable salt thereof.

A family of specific compounds of particular interest within Formula II consists of compounds and pharmaceutically-acceptable salts thereof as follows:

1-(2-phenylcyclopenten-1-yl)-4-(methylsulfonyl)benzene;
1-[2-(4-fluorophenyl)cyclopenten-1-yl]-4-(methylsulfonyl)benzene;
1-[2-(4-chlorophenyl)cyclopenten-1-yl]-4-(methylsulfonyl)benzene;
1-[2-(4-bromophenyl)cyclopenten-1-yl]-4-(methylsulfonyl)benzene;
1-[2-(4-iodophenyl)cyclopenten-1-yl]-4-(methylsulfonyl)benzene;
1-[2-(4-methylphenyl)cyclopenten-1-yl]-4-(methylsulfonyl)benzene;
1-[2-(4-ethylphenyl)cyclopenten-1-yl]-4 -(methylsulfonyl)benzene;
1-[2-(4-methoxyphenyl)cyclopenten-1-yl]-4-(methylsulfonyl)benzene;
1-[2-(4-methylthiophenyl)cyclopenten-1-yl]-4-(methylsulfonyl)benzene;
1-[2-(4-cyanophenyl)cyclopenten-1-yl]-4-(methylsulfonyl)benzene;
1-[2-(4-trifluoromethylphenyl)cyclopenten-1-yl]-4-(methylsulfonyl)benzene;
1-[2-(4-hydroxymethylphenyl)cyclopenten-1-yl]4-(methylsulfonyl)benzene;
1-[2-(4-methoxymethylphenyl)cyclopenten-1-yl]-4-(methylsulfonyl)benzene;
1-[2-(2,4-dimethylphenyl)cyclopenten-1-yl]-4-(methylsulfonyl)benzene;
1-[2-(2-methyl-4-fluorophenyl)cyclopenten-1-yl]-4-(methylsulfonyl)benzene;
1-[2-(2-methyl-4-chlorophenyl)cyclopenten-1-yl]-4-(methylsulfonyl)benzene;
1-[2-(2-fluoro-4-methylphenyl)cyclopenten-1-yl]-4-(methylsulfonyl)benzene;
1-[2-(2,4-difluorophenyl)cyclopenten-1-yl]-4-(methylsulfonyl)benzene;
1-[2-(2-fluoro-4-chlorophenyl)cyclopenten-1-yl]-4-(methylsulfonyl)benzene;
1-[2-(2-chloro-4-methylphenyl)cyclopenten-1-yl]-4-(methylsulfonyl)benzene;
1-[2-(2-chloro-4-fluorophenyl)cyclopenten-1-yl]-4-(methylsulfonyl)benzene;
1-[2-(2,4-dichlorophenyl)cyclopenten-1-yl]-4-(methylsulfonyl)benzene;
4-(2-phenylcyclopenten-1-yl ) benzenesulfonamide;
4-[2-(4-fluorophenyl)cyclopenten-1-yl]benzenesulfonamide;
4-[2-(4-chlorophenyl)cyclopenten-1-yl]benzenesulfonamide;
4-[2-(4-methylphenyl)cyclopenten-1-yl]benzenesulfonamide;
4-[2-(4-cyanophenyl)cyclopenten-1-yl]benzenesulfonamide;
4-[2-(4-trifluoromethylphenyl)cyclopenten-1-yl]benzenesulfonamide;
4-[2-(2,4-dimethylphenyl)cyclopenten-1-yl]benzenesulfonamide;
4-[2-(2-methyl-4-fluorophenyl)cyclopenten-1-yl]benzenesulfonamide;
4-[2-(2-methyl-4-chlorophenyl)cyclopenten-1-yl]benzenesulfonamide;
4-[2-(2-fluoro-4-methylphenyl)cyclopenten-1-yl]benzenesulfonamide;
4-[2-(2,4-difluorophenyl)cyclopenten-1-yl]benzenesulfonamide;
4-[2-(2-fluoro-4-chlorophenyl)cyclopenten-1-yl]benzenesulfonamide;
4-[2-(2-chloro-4-methylphenyl)cyclopenten-1-yl]benzenesulfonamide;
4-[2-(2-chloro-4-fluorophenyl)cyclopenten-1-yl]benzenesulfonamide;
4-[2-(2,4-dichlorophenyl)cyclopenten-1-yl]benzenesulfonamide;
1-[2-(4-fluorophenyl)-4,4-dimethylcyclopenten-1-yl]-4-(methylsulfonyl)benzene;
1-[2-(4-fluorophenyl)-4,4-diethylcyclopenten-1-yl]-4 -(methylsulfonyl)benzene;
1-[2-(4-fluorophenyl)-4,4-di(hydroxymethyl)cyclopenten-1-yl]-4-(methylsulfonyl)benzene;
1-[2-(4-fluorophenyl)-4,4-dicarbomethoxycyclopenten-1-yl]-4-(methylsulfonyl)benzene;
1-[2-(4-fluorophenyl)-4,4-difluorocyclopenten-1-yl]-4-(methylsulfonyl)benzene;
1-[2-(4-fluorophenyl)-4,4-di(trifluoromethyl)cyclopenten-1-yl]-4-(methylsulfonyl)benzene;
1-[2-(4-fluorophenyl)-4,4-di(fluoromethyl)cyclopenten-1-yl]-4-(methylsulfonyl)benzene;
1-[2-(4-trifluoromethylphenyl)-4,4-dimethylcyclopenten-1-yl]-4-(methylsulfonyl)benzene;
1-[2-(4-trifluoromethylphenyl)-4,4-diethylcyclopenten-1-yl]-4-(methylsulfonyl)benzene;
1-[2-(4-trifluoromethylphenyl)-4,4-di(hydroxymethyl)-cyclopenten-1-yl]-4-(methylsulfonyl)benzene;
1-[2-(4-trifluoromethylphenyl)-4,4-dicarbomethoxycyclopenten-1-yl]-4-(methylsulfonyl)benzene;
1-[2-(4-trifluoromethylphenyl)-4,4-difluorocyclopenten-1-yl]-4-(methylsulfonyl)benzene;
1-[2-(4-trifluoromethylphenyl)-4,4-di(trifluoromethyl)-cyclopenten-1-yl]-4-(methylsulfonyl)benzene;
1-[2-(4-trifluoromethylphenyl)-4,4-di(fluoromethyl)cyclopenten-1-yl]-4-(methylsulfonyl)benzene;
4-[2-(4-fluorophenyl)-4,4-dimethylcyclopenten-1-yl]benzenesulfonamide;
4-[2-(4-fluorophenyl)-4,4-diethylcyclopenten-1-yl]benzenesulfonamide;
4-[2-(4-fluorophenyl)-4,4-di(hydroxymethyl)cyclopenten-1-yl]benzenesulfonamide;
4-[2-(4-fluorophenyl)-4,4-dicarbomethoxycyclopenten-1-yl]benzenesulfonamide;
4-[2-(4-fluorophenyl)-4,4-difluorocyclopenten-1-yl]benzenesulfonamide;
4-[2-(4-fluorophenyl)-4,4-di(trifluoromethyl)cyclopenten-1-yl]benzenesulfonamide;

4-[2-(4-fluorophenyl)-4,4-di(fluoromethyl)cyclopenten-1-yl]benzenesulfonamide;

4-[2-(4-trifluoromethylphenyl)-4,4-dimethylcyclopenten-1-yl]benzenesulfonamide;

4-[2-(4-trifluoromethylphenyl)-4,4-diethylcyclopenten-1-yl]benzenesulfonamide;

4-[2-(4-trifluoromethylphenyl)-4,4-di(hydroxymethyl)cyclopenten-1-yl]benzenesulfonamide;

4-[2-(4-trifluoromethylphenyl)-4,4-dicarbomethoxycyclopenten-1-yl]benzenesulfonamide;

4-[2-(4-trifluoromethylphenyl)-4,4-difluorocyclopenten-1-yl]benzenesulfonamide;

4-[2-(4-trifluoromethylphenyl)-4,4-di(trifluoromethyl)cyclopenten-1-yl]benzenesulfonamide;

4-[2-(4-trifluoromethylphenyl)-4,4-di(fluoromethyl)cyclopenten-1-yl]benzenesulfonamide;

1-[2-(4-fluorophenyl)-4-methylcyclopenten-1-yl]-4-(methylsulfonyl)benzene;

1-[2-(4-fluorophenyl)-4-ethylcyclopenten-1-yl]-4-(methylsulfonyl)benzene;

1-[2-(4-fluorophenyl)-4-(hydroxymethyl)cyclopenten-1-yl]-4-(methylsulfonyl)benzene;

1-[2-(4-fluorophenyl)-4-carbomethoxycyclopenten-1-yl]-4-(methylsulfonyl)benzene;

1-[2-(4-fluorophenyl)-4-fluorocyclopenten-1-yl]-4-(methylsulfonyl)benzene;

1-[2-(4-fluorophenyl)-4-(trifluoromethylcyclopenten-1-yl]-4-(methylsulfonyl)benzene;

1-[2-(4-fluorophenyl)-4-carboxycyclopenten-1-yl]-4-(methylsulfonyl)benzene;

1-[2-(4-fluorophenyl)-4-(fluoromethyl)cyclopenten-1-yl]-4-(methylsulfonyl)benzene;

1-[2-(4-trifluoromethylphenyl)-4-methylcyclopenten-1-yl]-4-(methylsulfonyl)benzene;

1-[2-(4-trifluoromethylphenyl)-4-ethylcyclopenten-1-yl]-4-(methylsulfonyl)benzene;

1-[2-(4-trifluoromethylphenyl)-4-(hydroxymethyl)cyclopenten-1-yl]-4-(methylsulfonyl)benzene;

1-[2-(4-trifluoromethylphenyl)-4-carbomethoxycyclopenten-1-yl]-4-(methylsulfonyl)benzene;

1-[2-(4-trifluoromethylphenyl)-4-fluorocyclopenten-1-yl]-4-(methylsulfonyl)benzene;

1-[2-(4-trifluoromethylphenyl)-4-(trifluoromethyl)cyclopenten-1-yl]-4-(methylsulfonyl)benzene;

1-[2-(4-trifluoromethylphenyl)-4-carboxycyclopenten-1-yl]4-(methylsulfonyl)benzene;

1-[2-(4-trifluoromethylphenyl)-4-(fluoromethyl)cyclopenten-1-yl]-4-(methylsulfonyl)benzene;

1-[2-(2,4,6-trifluorophenyl)cyclopenten-1-yl]-4-(methylsulfonyl)benzene;

4-[2-(4-fluorophenyl)-4-methylcyclopenten-1-yl]benzenesulfonamide;

4-[2-(4-fluorophenyl)-4-ethylcyclopenten-1-yl]benzenesulfonamide; [4-(4-fluorophenyl)-4-(hydroxymethyl)cyclopenten-1-yl]benzenesulfonamide;

4-[2-(4-fluorophenyl)-4-carbomethoxycyclopenten-1-yl]benzenesulfonamide;

4-[2-(4-fluorophenyl)-4-fluorocyclopenten-1-yl]benzenesulfonamide;

4-[2-(4-fluorophenyl)-4-(trifluoromethyl)cyclopenten-1-yl]benzenesulfonamide;

4-[2-(4-fluorophenyl)-4-carboxycyclopenten-1-yl]benzenesulfonamide;

4-[2-(4-fluorophenyl)-4-(fluoromethyl)cyclopenten-1-yl]benzenesulfonamide;

4-[2-(4-trifluoromethylphenyl)-4-methylcyclopenten-1-yl]benzenesulfonamide;

4-[2-(4-trifluoromethylphenyl)-4-ethylcyclopenten-1-yl]benzenesulfonamide;

4-[2-(4-trifluoromethylphenyl)-4-(hydroxymethyl)cyclopenten-1-yl]benzenesulfonamide;

4-[2-(4-trifluoromethylphenyl)-4-carbomethoxycyclopenten-1-yl]benzenesulfonamide;

4-[2-(4-trifluoromethylphenyl)-4-fluorocyclopenten-1-yl]benzenesulfonamide;

4-[2-(4-trifluoromethylphenyl)-4-trifluoromethylcyclopenten-1-yl]benzenesulfonamide;

4-[2-(2,4,6-trifluorophenyl)cyclopenten-1-yl]benzenesulfonamide;

4-[2-(4-trifluoromethylphenyl)-4-carboxycyclopenten-1-yl]benzenesulfonamide; and 4-[2-(4-trifluoromethylphenyl)-4-(fluoromethyl)cyclopenten-1-yl]benzenesulfonamide.

A family of compounds of more particular interest within Formula II consists of compounds and their pharmaceutically-acceptable salts as follows:

1-[2-(4-fluorophenyl)cyclopenten-1-yl]-4-(methylsulfonyl)benzene;

1-[2-(4-fluoro-2-methylphenyl)cyclopenten-1-y]-4-(methylsulfonyl)benzene;

1-[2-(2,4-dichlorophenyl)cyclopenten-1-yl]-4-(methylsulfonyl)benzene;

1-[2-(4-chlorophenyl)cyclopenten-1-yl]-4-(methylsulfonyl)benzene;

1-[2-(4-trifluoromethylphenyl)cyclopenten-1-yl]-4-(methylsulfonyl)benzene;

1-[2-(4-methylphenyl)cyclopenten-1-yl]-4-(methylsulfonyl)benzene;

1-(2-phenylcyclopenten-1 -yl)-4-(methylsulfonyl)benzene;

1-[2-(4-cyanophenyl)cyclopenten-1-yl]-4-(methylsulfonyl)benzene;

1-[2-(4-hydroxymethylphenyl)cyclopenten-1-yl]-4-(methylsulfonyl)benzene;

1-[2-(4-methoxymethylphenyl)cyclopenten-1-yl]-4-(methylsulfonyl)benzene;

1-[2-(4-methylthiophenyl)cyclopenten-1-yl]-4-(methylsulfonyl)benzene;

1-[2-(4-fluorophenyl)-4,4-dimethylcyclopenten-1-yl]-4-(methylsulfonyl)benzene;

1-[2-(2,4,6-trifluorophenyl)-4,4-dimethylpent-1-yl]-4-(methylsulfonyl)benzene; and 4-[2-(2,4,6-trifluorophenyl)-4,4-dimethylcyclopenten-1-yl]benzenesulfonamide.

Within Formula I there is a second subclass of compounds of high interest represented by Formula III:

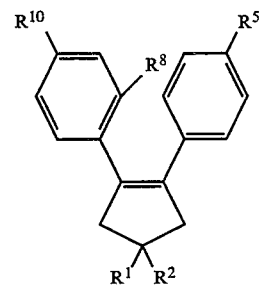

wherein each of $R^1$ and $R^2$ is independently selected from alkyl, hydrido, hydroxyalkyl, halo, haloalkyl, alkylcarboxyl and carboxyl; wherein $R^5$ is alkylsulfonyl or sulfamyl; wherein $R^8$ is selected from hydrido, alkyl and halo; and wherein $R^{10}$ is selected from hydrido, halo, alkyl, alkylthio, cyano, haloalkyl, alkoxy, hydroxyalkyl and alkoxyalkyl; or a pharmaceutically-acceptable salt thereof.

A class of compounds of particular interest consists of those compounds of Formula III wherein $R^1$ and $R^2$ are identical radicals selected from hydrido and methyl; wherein $R^5$ is methylsulfonyl or sulfamyl; wherein $R^8$ is selected from hydrido, methyl and chloro; and wherein $R^{10}$ is selected from hydrido, fluoro, chloro, methyl, methylthio, cyano, trifluoromethyl, hydroxymethyl and methoxymethyl; or a pharmaceutically-acceptable salt thereof.

Within Formula I there is a third subclass of compounds of high interest represented by Formula IV:

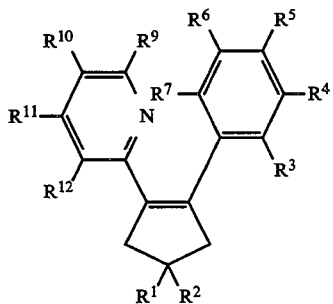

wherein each of $R^1$ and $R^2$ is independently selected from alkyl, hydrido, hydroxyalkyl, halo, haloalkyl, alkylcarboxyl and carboxyl; wherein each of $R^3$ through $R^7$ and $R^9$ through $R^{12}$ is independently selected from hydrido, halo, alkyl, cyano, haloalkyl, alkylsulfonyl and sulfamyl; provided that $R^5$ is selected from hydrido, halo, alkyl, cyano and haloalkyl, when $R^{10}$ is alkylsulfonyl or sulfamyl; and further provided that $R^{10}$ is selected from hydrido, halo, alkyl, cyano and haloalkyl where $R^5$ is alkylsulfonyl or sulfamyl; or a pharmaceutically-acceptable salt thereof.

A preferred class of compounds consists of those compounds of Formula IV wherein $R^1$ and $R^2$ are identical radicals selected from alkyl, hydrido, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein $R^5$ is alkylsulfonyl or sulfamyl; and wherein $R^{10}$ is selected from hydrido, halo, alkyl, cyano and haloalkyl; or a pharmaceutically-acceptable salt thereof.

A class of compounds of particular interest consists of those compounds of Formula IV wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein $R^5$ is methylsulfonyl or sulfamyl; and wherein $R^{10}$ is selected from hydrido, fluoro, chloro, methyl, cyano and trifluoromethyl; or a pharmaceutically-acceptable salt thereof.

Another preferred class of compounds consists of those compounds of Formula IV wherein $R^1$ and $R^2$ are identical radicals selected from alkyl, hydrido, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein $R^5$ is selected from hydrido, halo, alkyl, cyano and haloalkyl; and wherein $R^{10}$ is alkylsulfonyl or sulfamyl; or a pharmaceutically-acceptable salt thereof.

Another class of compounds of particular interest consists of those compounds of Formula IV wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein $R^5$ is selected from hydrido, fluoro, chloro, bromo, iodo, methyl, ethyl, methoxy, methylthio, cyano, trifluoromethyl, hydroxymethyl and methoxymethyl; and wherein $R^{10}$ is methylsulfonyl or sulfamyl; or a pharmaceutically-acceptable salt thereof.

A family of specific compounds of particular interest within Formula IV consists of compounds and pharmaceutically-acceptable salts thereof as follows:

2-[2-(4-(methylsulfonyl)phenyl]cyclopenten-1-yl]pyridine;

5-fluoro-2-[2-(4-(methylsulfonyl)phenyl]cyclopenten-1-yl]pyridine;

5-chloro-2-[2-(4-(methylsulfonyl)phenyl]cyclopenten-1-yl]pyridine;

5-methyl-2-[2-(4-(methylsulfonyl)phenyl]cyclopenten-1-yl]pyridine;

5-cyano-2-[2-(4-(methylsulfonyl)phenyl]cyclopenten-1-yl]pyridine;

5-trifluoromethyl-2-[2-(4-(methylsulfonyl)phenyl]cyclopenten-1-yl]pyridine;

4-[2-(pyridin-2-yl)cyclotpenten-1-yl]benzenesulfonamide;

4-[2-(5-fluoropyridin-2-yl)cyclopenten-1-yl]benzenesulfonamide

4-[2-(5-chloropyridin-2-yl)cyclopenten-1-yl]benzenesulfonamide

4-[2-(5-methylpyridin-2-yl)cyclopenten-1-yl]benzenesulfonamide

4-[2-(5-cyanopyridin-2-yl)cyclopenten-1-yl]benzenesulfonamide;

4-[2-(5-trifluoromethylpyridin-2-yl)cyclopenten-1-yl]benzenesulfonamide;

5-fluoro-2-[2-[4-(methylsulfonyl)phenyl]-4-methylcyclopenten-1-yl]pyridine;

5-fluoro-2-[2-[4-(methylsulfonyl)phenyl]-4-ethylcyclopenten-1-yl]pyridine;

5-fluoro-2-[2-[4-(methylsulfonyl)phenyl]-4-(hydroxymethyl)cyclopenten-1-yl]pyridine;

5-fluoro-2-[2-[4-(methylsulfonyl)phenyl]-4-carbomethoxycyclopenten-1-yl]pyridine;

5-fluoro-2-[2-[4-(methylsulfonyl)phenyl]-4-fluorocyclopenten-1-yl]pyridine;

5-fluoro-2-[2-[4-(methylsulfonyl)phenyl]-4-(trifluoromethyl)cyclopenten-1-yl]pyridine;

5-fluoro-2-[2-[4-(methylsulfonyl)phenyl]-4-carboxycyclopenten-1-yl]pyridine;

5-fluoro-2-[2-[4-(methylsulfonyl)phenyl]-4-(fluoromethyl)cyclopenten-1-yl]pyridine;

5-trifluoromethyl-2-[2-[4-(methylsulfonyl)phenyl]-4-methylcyclopenten-1-yl]pyridine;

5-trifluoromethyl-2-[2-[4-(methylsulfonyl)phenyl]-4-ethylcyclopenten-1-yl]pyridine;

5-trifluoromethyl-2-[2-[4-(methylsulfonyl)phenyl]-4-(hydroxymethyl)cyclopenten-1-yl]pyridine;

5-trifluoromethyl-2-[2-[4-(methylsulfonyl)phenyl]-4-carbomethoxycyclopenten-1-yl]pyridine;

5-trifluoromethyl-2-[2-[4-(methylsulfonyl)phenyl]-4-fluorocyclopenten-1-yl]pyridine;

5-trifluoromethyl-2-[2-[4-(methylsulfonyl)phenyl]-4-(trifluoromethyl)cyclopenten-1-yl]pyridine;
5-trifluoromethyl-2-[2-[4-(methylsulfonyl)phenyl]-4-carboxycyclopenten-1-yl]pyridine;
5-trifluoromethyl-2-[2-[4-(methylsulfonyl)phenyl]-4-(fluoromethyl)cyclopenten-1-yl]pyridine;
4-[2-(5-fluoropyridin-2-yl)-4-methylcyclopenten-1-yl]benzenesulfonamide;
4-[2-(5-fluoropyridin-2-yl)-4-ethylcyclopenten-1-yl]benzenesulfonamide;
4-[2-(5-fluoropyridin-2-yl)-4-(hydroxymethyl)cyclopenten-1-yl]benzenesulfonamide;
4-[2-(5-fluoropyridin-2-yl)-4-carbomethoxycyclopenten-1-yl]benzenesulfonamide;
4-[2-(5-fluoropyridin-2-yl)-4-fluorocyclopenten-1-yl]benzenesulfonamide;
4-[2-(5-fluoropyridin-2-yl)-4-(trifluoromethyl)cyclopenten-1-yl]benzenesulfonamide;
4-[2-(5-fluoropyridin-2-yl)-4-carboxycyclopenten-1-yl]benzenesulfonamide;
4-[2-(5-fluoropyridin-2-yl)-4-(fluoromethyl)cyclopenten-1-yl]benzenesulfonamide;
4-[2-(5-trifluoromethylpyridin-2-yl)-4-methylcyclopenten-1-yl]benzenesulfonamide;
4-[2-(5-trifluoromethylpyridin-2-yl)-4-ethylcyclopenten-1-yl]benzenesulfonamide;
4-[2-(5-trifluoromethylpyridin-2-yl)-4-(hydroxymethyl)cyclopenten-1-yl]benzenesulfonamide;
4-[2-(5-trifluoromethylpyridin-2-yl)-4-carbomethoxycyclopenten-1-yl]benzenesulfonamide;
4-[2-(5-trifluoromethylpyridin-2-yl)-4-fluorocyclopenten-1-yl]benzenesulfonamide;
4-[2-(5-trifluoromethylpyridin-2-yl)-4-(trifluoromethyl)cyclopenten-1-yl]benzenesulfonamide;
4-[2-(5-trifluoromethylpyridin-2-yl)-4-carboxycyclopenten-1-yl]benzenesulfonamide;
4-[2-(5-trifluoromethylpyridin-2-yl)-4-fluoromethylcyclopenten-1-yl]benzenesulfonamide;
5-fluoro-2-[2-[4-(methylsulfonyl)phenyl]-4,4-dimethylcyclopenten-1-yl]pyridine;
5-fluoro-2-[2-[4-(methylsulfonyl)phenyl]-4,4-diethylcyclopenten-1-yl]pyridine;
5-fluoro-2-[2-[4-(methylsulfonyl)phenyl]-4-di(hydroxymethyl)cyclopenten-1-yl]pyridine;
5-fluoro-2-[2-[4-(methylsulfonyl)phenyl]-4,4-dicarbomethoxycyclopenten-1-yl]pyridine;
5-fluoro-2-[2-[4-(methylsulfonyl)phenyl]-4,4-difluorocyclopenten-1-yl]pyridine;
5-fluoro-2-[2-[4-(methylsulfonyl)phenyl]-4,4-di(trifluoromethyl)cyclopenten-1-yl]pyridine;
5-fluoro-2-[2-[4-(methylsulfonyl)phenyl]-4,4-di(fluoromethyl)cyclopenten-1-yl]pyridine;
5-trifluoromethyl-2-[2-[4-(methylsulfonyl)phenyl]-4,4-dimethylcyclopenten-1-yl]pyridine;
5-trifluoromethyl-2-[2-[4-(methylsulfonyl)phenyl]-4,4-diethylcyclopenten-1-yl]pyridine;
5-trifluoromethyl-2-[2-[4-(methylsulfonyl)phenyl]-4,4-di(hydroxymethyl)cyclopenten-1-yl]pyridine;
5-trifluoromethyl-2-[2-[4-(methylsulfonyl)phenyl]-4,4-dicarbomethoxycyclopenten-1-yl]pyridine;
5-trifluoromethyl-2-[2-[4-(methylsulfonyl)phenyl]-4,4-difluorocyclopenten-1-yl]pyridine;
5-trifluoromethyl-2-[2-[4-(methylsulfonyl)phenyl]-4,4-di(trifluoromethyl)cyclopenten-1-yl]pyridine;
5-trifluoromethyl-2-[2-[4-(methylsulfonyl)phenyl]-4,4-di(fluoromethyl)cyclopenten-1-yl]pyridine;
4-[2-(5-fluoropyridin-2-yl)-4,4-dimethylcyclopenten-1-yl]benzenesulfonamide;
4-[2-(5-fluoropyridin-2-yl)-4,4-diethylcyclopenten-1-yl]benzenesulfonamide;
4-[2-(5-fluoropyridin-2-yl)-4,4-di(hydroxymethyl)cyclopenten-1-yl]benzenesulfonamide;
4-[2-(5-fluoropyridin-2-yl)-4,4-dicarbomethoxycyclopenten-1yl]benzenesulfonamide;
4-[2-(5-fluoropyridin-2-yl)-4,4-difluorocyclopenten-1-yl]benzenesulfonamide;
4-[2-(5-fluoropyridin-2-yl)-4,4-di(trifluoromethyl)cyclopenten-1-yl]benzenesulfonamide;
4-[2-(5-fluoropyridin-2-yl)-4,4-di(fluoromethyl)cyclopenten-1-yl]benzenesulfonamide;
4-[2-(5-trifluoromethylpyridin-2-yl)-4,4-dimethylcyclopenten-1-yl]benzenesulfonamide;
4-[2-(5-trifluoromethylpyridin-2-yl)-4,4-diethylcyclopenten-1-yl ]benzenesulfonamide;
4-[2-(5-trifluoromethylpyridin-2-yl)-4,4-di(hydroxymethyl)cyclopenten-1-yl]benzenesulfonamide;
4-[2-(5-trifluoromethylpyridin-2-yl)-4,4-dicarbomethoxycyclopenten-1-yl]benzenesulfonamide;
4-[2-(5-trifluoromethylpyridin-2-yl)-4,4-difluorocyclopenten-1-yl]benzenesulfonamide
4-[2-(5-trifluoromethylpyridin-2-yl)-4,4-di(trifluoromethyl)cyclopenten-1-]benzenesulfonamide;
4-[2-(5-trifluoromethylpyridin-2-yl)-4,4-di(fluoromethyl)cyclopenten-1-yl]benzenesulfonamide;
2-[2-phenylcyclopenten-1-yl]-5(methylsulfonyl)pyridine;
2-[2-(4-fluorophenyl)cyclopenten-1-yl]-5-(methylsulfonyl)pyridine;
2-[2-(4-chlorophenyl)cyclopenten-1-yl]-5-(methylsulfonyl)pyridine;
2-[2-(4-methylphenyl)cyclopenten-1-yl]-5-(methylsulfonyl)pyridine;
2-[2-(4-cyanophenyl)cyclopenten-1-yl]-5- (methylsulfonyl)pyridine;
2-[2-(4-trifluoromethylphenyl)cyclopenten-1-yl]-5-(methylsulfonyl)pyridine;
2-[2-phenylcyclopenten-1-yl]pyridine-5-sulfonamide;
2-[2-(4-fluorophenyl)cyclopenten-1-yl]pyridine-5-sulfonamide;
2-[2-(4-chlorophenyl)cyclopenten-1-yl]pyridine-5-sulfonamide;
2-[2-(4-methylphenyl)cyclopenten-1-yl]pyridine-5-sulfonamide;
2-[2-(4-cyanophenyl)cyclopenten-1-yl]pyridine-5-sulfonamide;
2-[2-(4-trifluoromethylphenyl)cyclopenten-1-yl]pyridine-5-sulfonamide;
2-[2-(4-fluorophenyl)-4-methylcyclopenten-1-yl]-5-(methylsulfonyl)pyridine;
2-[2-(4-fluorophenyl)-4-ethylcyclopenten-1-yl]-5-(methylsulfonyl)pyridine;
2-[2-(4-fluorophenyl)-4-(hydroxymethyl)cyclopenten-1-yl]-5-(methylsulfonyl)pyridine;
2-[2-(4-fluorophenyl)-4-fluorocyclopenten-1-yl]-5-(methylsulfonyl)pyridine;
2-[2-(4-fluorophenyl)-4-(trifluoromethyl)cyclopenten-1-yl]-5-(methylsulfonyl)pyridine;
2-[2-(4-fluorophenyl)-4-carboxycyclopenten-1-yl]-5-(methylsulfonyl)pyridine;
2-[2-(4-fluorophenyl)-4-(fluoromethyl)cyclopenten-1-yl]-5-(methylsulfonyl)pyridine;
2-[2-(4-trifluoromethylphenyl)-4-methylcyclopenten-1-yl]-5-(methylsulfonyl)pyridine;
2-[2-(4-trifluoromethylphenyl)-4-ethylcyclopenten-1-yl]-5-(methylsulfonyl)pyridine;

2-[2-(4-trifluoromethylphenyl)-4-(hydroxymethyl)cyclopenten-1-yl]-5-(methylsulfonyl)pyridine;
2-[2-(4-trifluoromethylphenyl)-4-carbomethoxycyclopenten-1-yl]-5-(methylsulfonyl)pyridine;
2-[2-(4-trifluoromethylphenyl)-4-fluorocyclopenten-1-yl]-5-(methylsulfonyl)pyridine;
2-[2-(4-trifluoromethylphenyl)-4-carboxycyclopenten-1-yl]-5-(methylsulfonyl)pyridine;
2-[2-(4-trifluoromethylphenyl)-4-(trifluoromethyl)cyclopenten-1-yl]-5-(methylsulfonyl)pyridine;
2-[2-(4-fluorophenyl)-4-methylcyclopenten-1-yl]pyridine-5-sulfonamide;
2-[2-(4-fluorophenyl)-4-ethylcyclopenten-1-yl]pyridine-5-sulfonamide;
2-[2-(4-fluorophenyl)-4-(hydroxymethyl)cyclopenten-1-yl]pyridine-5-sulfonamide;
2-[2-(4-fluorophenyl)-4-carbomethoxycyclopenten-1-yl]pyridine-5-sulfonamide;
2-[2-(4-fluorophenyl)-4-fluorocyclopenten-1-yl]pyridine-5-sulfonamide;
2-[2-(4-fluorophenyl)-4-(trifluoromethyl)cyclopenten-1-yl]pyridine-5-sulfonamide;
2-[2-(4-fluorophenyl)-4-carboxycyclopenten-1-yl]pyridine-5-sulfonamide;
2-[2-(4-fluorophenyl)-4-(fluoromethyl)cyclopenten-1-yl]pyridine-5-sulfonamide;
2-[2-(4-trifluoromethylphenyl)-4-methylcyclopenten-1-yl]pyridine-5-sulfonamide;
2-[2-(4-trifluoromethylphenyl)-4-ethylcyclopenten-1-yl]pyridine-5-sulfonamide;
2-[2-(4-trifluoromethylphenyl)-4-(hydroxymethyl)cyclopenten-1-yl]pyridine-5-sulfonamide;
2-[2-(4-trifluoromethylphenyl)-4-carbomethoxycyclopenten-1-yl]pyridine-5-sulfonamide;
2-[2-(4-trifluoromethylphenyl)-4-fluorocyclopenten-1-yl]pyridine-5-sulfonamide;
2-[2-(4-trifluoromethylphenyl)-4-(trifluoromethyl)cyclopenten-1-yl]pyridine-5-sulfonamide;
2-[2-(4-trifluoromethylphenyl)-4-carboxycyclopenten-1-yl]pyridine-5-sulfonamide;
2-[2-(4-trifluoromethylphenyl)-4-(fluoromethyl)cyclopenten-1-yl]pyridine-5-sulfonamide;
2-[2-(4-fluorophenyl)-4,4-dimethylcyclopenten-1-yl]-5-(methylsulfonyl)pyridine;
2-[2-(4-fluorophenyl)-4,4-diethylcyclopenten-1-yl]-5-(methylsulfonyl)pyridine;
2-[2-(4-fluorophenyl)-4,4-di(hydroxymethyl)cyclopenten-1-yl]-5-(methylsulfonyl)pyridine;
2-[2-(4-fluorophenyl)-4,4-dicarbomethoxycyclopenten-1-yl]-5-(methylsulfonyl)pyridine;
2-[2-(4-fluorophenyl)-4,4-difluorocyclopenten-1-yl]-5-(methylsulfonyl)pyridine;
2-[2-(4-fluorophenyl)-4,4-di(trifluoromethyl)cyclopenten-1-yl]-5-(methylsulfonyl)pyridine;
2-[2-(4-fluorophenyl)-4,4-di(fluoromethyl)cyclopenten-1-yl]-5-(methylsulfonyl)pyridine;
2-[2-(4-trifluoromethylphenyl)-4,4-dimethylcyclopenten-1-yl]-5-(methylsulfonyl)pyridine;
2-[2-(4-trifluoromethylphenyl)-4,4-diethylcyclopenten-1-yl]-5-(methylsulfonyl)pyridine;
2-[2-(4-trifluoromethylphenyl)-4,4-di(hydroxymethyl)cyclopenten-1-yl]-5-(methylsulfonyl)pyridine;
2-[2-(4-trifluoromethylphenyl)-4,4-dicarbomethoxycyclopenten-1-yl]-5-(methylsulfonyl)pyridine;
2-[2-(4-trifluoromethylphenyl)-4,4-difluorocyclopenten-1-yl]-5-(methylsulfonyl)pyridine;
2-[2-(4-trifluoromethylphenyl)-4,4-di(trifluoromethyl)cyclopenten-1-yl]-5-(methylsulfonyl)pyridine;
2-[2-(4-trifluoromethylphenyl)-4,4-di(fluoromethyl)cyclopenten-1-yl]-5-(methylsulfonyl)pyridine;
2-[2-(4-fluorophenyl)-4,4-dimethylcyclopenten-1-yl]pyridine-5-sulfonamide;
2-[2-(4-fluorophenyl)-4,4-diethylcyclopenten-1-yl]pyridine-5-sulfonamide;
2-[2-(4-fluorophenyl)-4,4-di(hydroxymethyl)cyclopenten-1-yl]pyridine-5-sulfonamide;
2-[2-(4-fluorophenyl)-4,4-dicarbomethoxycyclopenten-1-yl]pyridine-5-sulfonamide;
2-[2-(4-fluorophenyl)-4,4-difluorocyclopenten-1-yl]pyridine-5-sulfonamide;
2-[2-(4-fluorophenyl)-4,4-di(trifluoromethyl)cyclopenten-1-yl]pyridine-5-sulfonamide;
2-[2-(4-fluorophenyl)-4,4-di(fluoromethyl)cyclopenten-1-yl-]pyridine-5-sulfonamide;
2-[2-(4-trifluoromethylphenyl)-4,4-dimethylcyclopenten-1-yl]pyridine-5-sulfonamide;
2-[2-(4-trifluoromethylphenyl)-4,4-diethylcyclopenten-1-yl]pyridine-5-sulfonamide;
2-[2-(4-trifluoromethylphenyl)-4,4-di(hydroxymethyl)-cyclopenten-1-yl]pyridine-5-sulfonamide;
2-[2-(4-trifluoromethylphenyl)-4,4-dicarbomethoxycyclopenten-1-yl]pyridine-5-sulfonamide;
2-[2-(4-trifluoromethylphenyl)-4,4-difluorocyclopenten-1-yl]pyridine-5-sulfonamide
2-[2-(4-trifluoromethylphenyl)-4,4-di(trifluoromethyl)-cyclopenten-1-yl]pyridine-5-sulfonamide; and
2-[2-(4-trifluoromethylphenyl)-4,4-di(fluoromethyl)cyclopenten-1-yl]pyridine-5-sulfonamide.

Within Formula I there is a fourth subclass of compounds of high interest represented by Formula V:

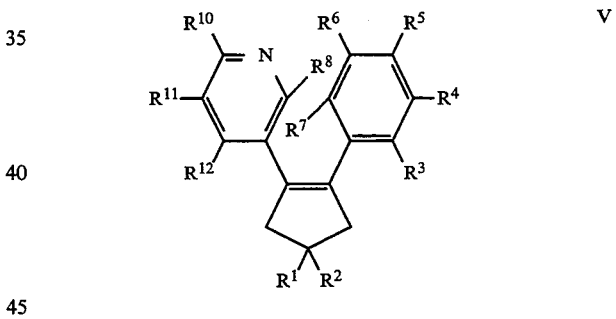

wherein each of $R^1$ and $R^2$ is independently selected from alkyl, hydrido, hydroxyalkyl, halo, haloalkyl, alkylcarboxyl and carboxyl; wherein each of $R^3$ through $R^7$, $R^8$, $R^{10}$, $R^{11}$ and $R^{12}$ is independently selected from hydrido, halo, alkyl, cyano, haloalkyl, alkylsulfonyl and sulfamyl; provided that $R^5$ is selected from hydrido, halo, alkyl, cyano and haloalkyl, when $R^{10}$ is alkylsulfonyl or sulfamyl; and further provided that $R^{10}$ is selected from hydrido, halo, alkyl, cyano and haloalkyl when $R^5$ is alkylsulfonyl or sulfamyl; or a pharmaceutically-acceptable salt thereof.

A preferred class of compounds consists of those compounds of Formula V wherein $R^1$ and $R^2$ are identical radicals selected from alkyl, hydrido, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein $R^5$ is alkylsulfonyl and sulfamyl; and wherein $R^{10}$ is selected from hydrido, halo, alkyl, cyano and haloalkyl; or a pharmaceutically-acceptable salt thereof.

A class of compounds of particular interest consists of those compounds of Formula V wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, ethyl, fluoro, hydroxymethyl, carbomethoxy, trifluoromethyl, carboxyl and fluoromethyl; wherein $R^5$ is methylsulfonyl or sulfamyl; and wherein $R^{10}$ is selected from hydrido, fluoro, chloro, bromo, iodo, methyl, ethyl, methoxy, methylthio, cyano, trifluoromethyl, hydroxymethyl and methoxymethyl; or a pharmaceutically-acceptable salt thereof.

Another preferred class of compounds consists of those compounds of Formula V wherein $R^1$ and $R^2$ are identical radicals selected from alkyl, hydrido, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein $R^5$ is selected from hydrido, halo, alkyl, cyano and haloalkyl; and wherein $R^{10}$ is alkylsulfonyl and sulfamyl; or a pharmaceutically-acceptable salt thereof.

Another class of compounds of particular interest consists of those compounds of Formula V wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein $R^5$ is selected from hydrido, fluoro, chloro, bromo, iodo, methyl, ethyl, methoxy, methylthio, cyano, trifluoromethyl, hydroxymethyl and methoxymethyl; and wherein $R^{10}$ is methylsulfonyl or sulfamyl; or a pharmaceutically-acceptable salt thereof.

A family of specific compounds of particular interest within Formula V consists of compounds and pharmaceutically-acceptable salts thereof as follows:

5-[2-[b 4-(methylsulfonyl)phenyl]cyclopenten-1-yl]pyridine;
2-fluoro-5-[2-[4-(methylsulfonyl)phenyl]cyclopenten-1-yl]pyridine;
2-chloro-5-[2-[4-(methylsulfonyl)phenyl]cyclopenten-1-yl]pyridine;
2-methyl-5-[2-[4-(methylsulfonyl)phenyl]cyclopenten-1-yl]pyridine;
2-cyano-5-[2-[4-(methylsulfonyl)phenyl]cyclopenten-1-yl]pyridine;
2-trifluoromethyl-5-[2-[4-(methylsulfonyl)phenyl]cyclopenten-1-yl]pyridine;
4-[2-(pyridin-5-yl)cyclopenten-1-yl]benzenesulfonamide;
4-[2-(2-fluoropyridin-5-yl)cyclopenten-1-yl]benzenesulfonamide;
4-[2-(2-chloropyridin-5-yl)cyclopenten-1-yl]benzenesulfonamide;
4-[2-(2-methylpyridin-5-yl)cyclopenten-1-yl]benzenesulfonamide;
4-[2-(2-cyanopyridin-5-yl) cyclopenten-1-yl ]benzenesulfonamide;
4-[2-(2-trifluoromethylpyridin-5-yl)cyclopenten-1-yl]benzenesulfonamide;
2-fluoro-5-[2-[4-(methylsulfonyl)phenyl]-4-methylcyclopenten-1-yl]pyridine;
2-fluoro-5-[2-[4-(methylsulfonyl)phenyl]-4-ethycyclopenten-1-yl ]pyridine;
2-fluoro-5-[2-[4-(methylsulfonyl)phenyl]-4-(hydroxymethyl)cyclopenten-1-yl]pyridine;
2-fluoro-5-[2-[4-(methylsulfonyl)phenyl]-4-carbomethoxycyclopenten-1-yl]pyridine;
2-fluoro-5-[2-[4-(methylsulfonyl)phenyl]-4-fluorocyclopenten-1-yl]pyridine;
2-fluoro-5-[2-[4-(methylsulfonyl)phenyl]-4-(trifluoromethyl)cyclopenten-1-yl]pyridine;
2-fluoro-5-[2-[4-(methylsulfonyl)phenyl]-4-carboxycyclopenten-1-yl]pyridine;
2-fluoro-5-[2-[4-(methylsulfonyl)phenyl]-4-(fluoromethyl)cyclopenten-1-yl]pyridine;
2-trifluoromethyl-5-[2-[4-(methylsulfonyl)phenyl]-4-methylcyclopenten-1-yl]pyridine;
2-trifluoromethyl-5-[2-[4-(methylsulfonyl)phenyl]-4-ethylcyclopenten-1-yl]pyridine;
2-trifluoromethyl-5-[2-[4-(methylsulfonyl)phenyl]-4-(hydroxymethyl)cyclopenten-1-yl]pyridine;
2-trifluoromethyl-5-[2-[4-(methylsulfonyl)phenyl]-4-carbomethoxycyclopenten-1-yl]pyridine;
2-trifluoromethyl-5-[2-[4-(methylsulfonyl)phenyl]-4-fluorocyclopenten-1-yl ]pyridine;
2-trifluoromethyl-5-[2-[4-(methylsulfonyl)phenyl]-4-(trifluoromethyl)cyclopenten-1-yl]pyridine;
2-trifluoromethyl-5-[2-[4-(methylsulfonyl)phenyl]-4-carboxycyclopenten-1-yl]pyridine;
2-trifluoromethyl-5-[2-[4-(methylsulfonyl)phenyl]-4-(fluoromethyl)cyclopenten-1-yl]pyridine;
4-[2-(2-fluoropyridin-5-yl)-4-methylcyclopenten-1-yl]benzenesulfonamide;
4-[2-(2-fluoropyridin-5-yl)-4-ethylcyclopenten-1-yl]benzenesulfonamide;
4-[2-(2-fluoropyridin-5-yl)-4-(hydroxymethyl)cyclopenten-1-yl]benzenesulfonamide;
4-[2-(2-fluoropyridin-5-yl)-4-carbomethoxycyclopenten-1-yl]benzenesulfonamide;
4-[2-(2-fluoropyridin-5-yl)-4-fluorocyclopenten-1-yl]benzenesulfonamide;
4-[2-(2-fluoropyridin-5-yl)-4-(trifluoromethyl)cyclopenten-1yl]benzenesulfonamide;
4-[2-(2-fluoropyridin-5-yl)-4-carboxycyclopenten-1-yl]benzenesulfonamide;
4-[2-(2-fluoropyridin-5-yl)-4-(fluoromethyl)cyclopenten-1-yl]benzenesulfonamide;
4-[2-(2-trifluoromethyl-5-[2-[4-(methylsulfonyl)phenyl]-4,4 -dimethylcyclopenten-1-yl]pyridine;
4-[2-(2 -trifluoromethyl-5-[2-[4-(methylsulfonyl)phenyl]-4,4-diethylcyclopenten-1-yl]pyridine;
4-[2-(2-trifluoromethyl-5-[2-[4-(methylsulfonyl)phenyl]-4,4-di(hydroxymethyl)cyclopenten-1-yl]pyridine;
4-[2-(2-trifluoromethyl-5-[2-[4-(methylsulfonyl)phenyl]-4,4-dicarbomethoxycyclopenten-1-yl]pyridine;
4-[2-(2-trifluoromethyl-5-[2-[4-(methylsulfonyl)phenyl]-4,4-difluorocyclopenten-1-yl ]pyridine;
4-[2-(2-trifluoromethyl-5-[2-[4-(methylsulfonyl)phenyl]-4,4-di(trifluoromethyl)cyclopenten-1-yl]pyridine;
4-[2-(2-trifluoromethyl-5-[2-[4-(methylsulfonyl)phenyl]-4,4-dicarboxycyclopenten-1-yl]pyridine;
4-[2-(2-trifluoromethyl-5-[2-[4-(methylsulfonyl)phenyl]-4,4 -difluoromethylcyclopenten-1-yl]pyridine;
2-fluoro-5-[2-[4-(methylsulfonyl)phenyl]-4,4-dimethylcyclopenten-1-yl]pyridine;
2-fluoro-5-[2-[4-(methylsulfonyl)phenyl]-4,4-diethylcyclopenten-1-yl]pyridine;
2-fluoro-5-[2-[4-(methylsulfonyl)phenyl]-4,4-di(hydroxymethyl)cyclopenten-1-yl]pyridine;

2-fluoro-5-[2-[4-(methylsulfonyl)phenyl]-4,4-dicarbomethoxycyclopenten-1-yl]pyridine;
2-fluoro-5-[2-[4-(methylsulfonyl)phenyl]-4,4-difluorocyclopenten-1-yl]pyridine;
2-fluoro-5-[2-[4-(methylsulfonyl)phenyl]-4,4-di(trifluoromethyl)cyclopenten-1-yl]pyridine;
2-fluoro-5-[2-[4-(methylsulfonyl)phenyl]-4,4-di(fluoromethyl)cyclopenten-1-yl]pyridine;
2-trifluoromethyl-5-[2-[4-(methylsulfonyl)phenyl]-4,4-dimethylcyclopenten-1-yl]pyridine;
2-trifluoromethyl-5-[2-[4-(methylsulfonyl)phenyl]-4,4-diethylcyclopenten-1-yl]pyridine;
2-trifluoromethyl-5-[2-[4-(methylsulfonyl)phenyl]-4,4-di(hydroxymethyl)cyclopenten-1-yl]pyridine;
2-trifluoromethyl-5-[2-[4-(methylsulfonyl)phenyl]-4,4-dicarbomethoxycyclopenten-1-yl]pyridine;
2-trifluoromethyl-5-[2-[4-(methylsulfonyl)phenyl]-4,4-difluorocyclopenten-1-yl]pyridine;
2-trifluoromethyl-5-[2-[4-(methylsulfonyl)phenyl]-4,4-di(trifluoromethyl)cyclopenten-1-yl]pyridine;
2-trifluoromethyl-5-[2-[4-(methylsulfonyl)phenyl]-4,4-di(fluoromethyl)cyclopenten-1-yl]pyridine;
4-[2-(2-fluoropyridin-5-yl)-4,4-dimethylcyclopenten-1-yl]benzenesulfonamide;
4-[2-(2-fluoropyridin-5-yl)-4,4-diethylcyclopenten-1-yl]benzenesulfonamide;
4-[2-(2-fluoropyridin-5-yl)-4,4-di(hydroxymethyl)cyclopenten-1-yl]benzenesulfonamide;
4-[2-(2-fluoropyridin-5-yl)-4,4-dicarbomethoxycyclopenten-1-yl]benzenesulfonamide;
4-[2-(2-fluoropyridin-5-yl)-4,4-difluorocyclopenten-1-yl]benzenesulfonamide;
4-[2-(2-fluoropyridin-5-yl)-4,4-di(trifluoromethyl)cyclopenten-1-1]benzenesulfonamide;
4-[2-(2-fluoropyridin-5-yl)-4,4-di(fluoromethyl)cyclopenten-1-yl]benzenesulfonamide;
4-[2-(2-trifluoromethylpyridin-5-yl)-4,4-dimethylcyclopenten-1-yl]benzenesulfonamide;
4-[2-(2-trifluoromethylpyridin-5-yl)-4,4-diethylcyclopenten-1-yl]benzenesulfonamide;
4-[2-(2-trifluoromethylpyridin-5-yl)-4,4-di(hydroxymethyl)cyclopenten-1-yl]benzenesulfonamide;
4-[2-(2-trifluoromethylpyridin-5-yl)-4,4-dicarbomethoxycyclopenten-1-yl]benzenesulfonamide;
4-[2-(2-trifluoromethylpyridin-5-yl)-4,4-difluorocyclopenten-1-yl]benzenesulfonamide
4-[2-(2-trifluoromethylpyridin-5-yl)-4,4-di(trifluoromethyl)cyclotpenten-1-]benzenesulfonamide;
4-[2-(2-trifluoromethylpyridin-5-yl)-4,4-di(fluoromethyl)cyclopenten-1-yl]benzenesulfonamide;
5-(2-phenylcyclopenten-1-yl)-2-(methylsulfonyl)pyridine;
5-[2-(4-fluorophenyl)cyclopenten-1-yl]-2-(methylsulfonyl)pyridine;
5-[2-(4-chlorophenyl)cyclopenten-1-yl]-2-(methylsulfonyl)pyridine;
5-[2-(4-methylphenyl)cyclopenten-1-yl]-2-(methylsulfonyl)pyridine;
5-[2-(4-cyanophenyl)cyclopenten-1-yl]-2-(methylsulfonyl)pyridine;
5-[2-(4-trifluoromethylphenyl)cyclopenten-1-yl]-2-(methylsulfonyl)pyridine;
5-(2-phenylcyclopenten-1-yl)pyridine-2-sulfonamide;
5-[2-(4-fluorophenyl)cyclopenten-1-yl]pyridine-2-sulfonamide;
5-[2-(4-chlorophenyl)cyclopenten-1-yl]pyridine-2-sulfonamide;
5-[2-(4-methylphenyl)cyclopenten-1-yl]pyridine-2-sulfonamide;
5-[2-(4-cyanophenyl)cyclopenten-1-yl]pyridine-2-sulfonamide;
5-[2-(4-trifluoromethylphenyl)cyclopenten-1-yl]pyridine-2-sulfonamide;
5-[2-(4-fluorophenyl)-4-methylcyclopenten-1-yl]-2-(methylsulfonyl)pyridine;
5-[2-(4-fluorophenyl)-4-ethylcyclopenten-1-yl]-2-(methylsulfonyl)pyridine;
5-[2-(4-fluorophenyl)-4-(hydroxymethyl)cyclopenten-1-yl]-2-(methylsulfonyl)pyridine;
5-[2-(4-fluorophenyl)-4-carbomethoxycyclopenten-1-yl]-2-(methylsulfonyl)pyridine;
5-[2-(4-fluorophenyl)-4-fluorocyclopenten-1-yl]-2-(methylsulfonyl)pyridine;
5-[2-(4-fluorophenyl)-4-(trifluoromethyl)cyclopenten-1-yl]-2-(methylsulfonyl)pyridine;
5-[2-(4-fluorophenyl)-4-carboxycyclopenten-1-yl]-2-(methylsulfonyl)pyridine;
5-[2-(4-fluorophenyl)-4-(fluoromethyl)cyclopenten-1-yl]-2-(methylsulfonyl)pyridine;
5-[2-(4-trifluoromethylphenyl)-4-methylcyclopenten-1-yl]-2-(methylsulfonyl)pyridine;
5-[2-(4-trifluoromethylphenyl)-4-ethylcyclopenten-1-yl]-2-(methylsulfonyl)pyridine;
5-[2-(4-trifluoromethylphenyl)-4-(hydroxymethyl)cyclopenten-1-yl]-2-(methylsulfonyl)pyridine;
5-[2-(4-trifluoromethylphenyl)-4-carbomethoxycyclopenten-1-yl]-2-(methylsulfonyl)pyridine;
5-[2-(4-trifluoromethylphenyl)-4-fluorocyclopenten-1-yl]-2-(methylsulfonyl)pyridine;
5-[2-(4-trifluoromethylphenyl)-4-(trifluoromethyl)cyclopenten-1-yl]-2-(methylsulfonyl)pyridine;
5-[2-(4-trifluoromethylphenyl)-4-carboxycyclopenten-1-yl]-2-(methylsulfonyl)pyridine;
5-[2-(4-trifluoromethylphenyl)-4-(fluoromethyl)cyclopenten-1-yl]-2-(methylsulfonyl)pyridine;
5-[2-(4-fluorophenyl)-4-methylcyclopenten-1-yl]pyridine-2-sulfonamide;
5-[2-(4-fluorophenyl)-4-ethylcyclopenten-1-yl]pyridine-2-sulfonamide;
5-[2-(4-fluorophenyl)-4-(hydroxymethyl)cyclopenten-1-yl]pyridine-2-sulfonamide;
5-[2-(4-fluorophenyl)-4-carbomethoxycyclopenten-1-yl]pyridine-2-sulfonamide;
5-[2-(4-fluorophenyl)-4-fluorocyclopenten-1-yl]pyridine-2-sulfonamide;
5-[2-(4-fluorophenyl)-4-(trifluoromethyl)cyclopenten-1-yl]pyridine-2-sulfonamide;
5-[2-(4-fluorophenyl)-4-carboxycyclopenten-1-yl]pyridine-2-sulfonamide;
5-[2-(4-fluorophenyl)-4-(fluoromethyl)cyclopenten-1-yl]pyridine-2-sulfonamide;
5-[2-(4-trifluoromethylphenyl)-4-methylcyclopenten-1-yl]pyridine-2-sulfonamide
5- 8 2-(4-trifluoromethylphenyl)-4-ethylcyclopenten-1-yl]pyridine-2-sulfonamide
5-[2-(4-trifluoromethylphenyl)-4-(hydroxymethyl)cyclopenten-1-yl]pyridine-2-sulfonamide;
5-[2-(4-trifluoromethylphenyl)-4-carbomethoxycyclopenten-1-yl]pyridine-2-sulfonamide
5-[2-(4-trifluoromethylphenyl)-4-fluorocyclopenten-1-yl]pyridine-2-sulfonamide
5-[2-(4-trifluoromethylphenyl)-4-(trifluoromethyl)cyclopenten-1-yl]pyridine-2-sulfonamide;
5-[2-(4-trifluoromethylphenyl)-4-carboxycyclopenten-1-yl]pyridine-2-sulfonamide 5-[2-(4-trifluoromethylphenyl)-4-(fluoromethyl)cyclopenten-1-yl]pyridine-2-sulfonamide;
5-[2-(4-fluorophenyl)-4,4-dimethylcyclopenten-1-yl]-2-(methylsulfonyl)pyridine;
5-[2-(4-fluorophenyl)-4,4-diethylcyclopenten-1-yl]-2-(methylsulfonyl)pyridine;
5-[2-(4-fluorophenyl)-4,4-di(hydroxymethyl)cyclopenten-1-yl]-2-(methylsulfonyl)pyridine;
5-[2-(4-fluorophenyl)-4,4-dicarbomethoxycyclopenten-1-yl]-2-(methylsulfonyl)pyridine;
5-[2-(4-fluorophenyl)-4,4-difluorocyclopenten-1-yl]-2-(methylsulfonyl)pyridine;
5-[2-(4-fluorophenyl)-4,4-di(trifluoromethyl)cyclopenten-1-yl]-2-(methylsulfonyl)pyridine;
5-[2-(4-fluorophenyl)-4,4-di(fluoromethyl)cyclopenten-1-yl]-2-(methylsulfonyl)pyridine;
5-[2-(4-trifluoromethylphenyl)-4,4-dimethylcyclopenten-1-yl]-2-(methylsulfonyl)pyridine;
5-[2-(4-trifluoromethylphenyl)-4,4-diethylcyclopenten-1-yl]-2-(methylsulfonyl)pyridine;
5-[2-(4-trifluoromethylphenyl)-4,4-di(hydroxymethyl)cyclopenten-1-yl]-2-(methylsulfonyl)pyridine;
5-[2-(4-trifluoromethylphenyl)-4,4-dicarbomethoxycyclopenten-1-yl]-2-(methylsulfonyl)pyridine;
5-[2-(4-trifluoromethylphenyl)-4,4-difluorocyclopenten-1-yl]-2-(methylsulfonyl)pyridine;
5-[2-(4-trifluoromethylphenyl)-4,4-di(trifluoromethyl)cyclopenten-1-yl]-2-(methylsulfonyl)pyridine;
5-[2-(4-trifluoromethylphenyl)-4,4-di(fluoromethyl)cyclopenten-1-yl]-2-(methylsulfonyl)pyridine;
5-[2-(4-fluorophenyl)-4,4-dimethylcyclopenten-1-yl]pyridine-2-sulfonamide;
5-[2-(4-fluorophenyl)-4,4-diethylcyclopenten-1-yl]pyridine-2-sulfonamide;
5-[2-(4-fluorophenyl)-4,4-di(hydroxymethyl)cyclopenten-1-yl]pyridine-2-sulfonamide;
5-[2-(4-fluorophenyl)-4,4-dicarbomethoxycyclopenten-1-yl]pyridine-2-sulfonamide;
5-[2-(4-fluorophenyl)-4,4-difluorocyclopenten-1-yl]pyridine-2-sulfonamide;
5-[2-(4-fluorophenyl)-4,4-di(trifluoromethyl)cyclopenten-1-yl]pyridine-2-sulfonamide;
5-[2-(4-fluorophenyl)-4,4-di(fluoromethyl)cyclopenten-1-yl]pyridine-2-sulfonamide;
5-[2-(4-trifluoromethylphenyl)-4,4-dimethylcyclopenten-1-yl]pyridine-2-sulfonamide;
5-[2-(4-trifluoromethylphenyl)-4,4-diethylcyclopenten-1-yl]pyridine-2-sulfonamide;
5-[2-(4-trifluoromethylphenyl)-4,4-di(hydroxymethyl)cyclopenten-1-yl]pyridine-2-sulfonamide;
5-[2-(4-trifluoromethylphenyl)-4,4-dicarbomethoxycyclopenten-1-yl]pyridine-2-sulfonamide;
5-[2-(4-trifluoromethylphenyl)-4,4-difluorocyclopenten-1-yl]pyridine-2 -sulfonamide;
5-[2-(4-trifluoromethylphenyl)-4,4-di(trifluoromethyl)cyclopenten-1-yl]pyridine-2-sulfonamide; and
5-[2-(4-trifluoromethylphenyl)-4,4-di(fluoromethyl)cyclopenten-1-yl]pyridine-2-sulfonamide.

Within Formula I there is a fifth subclass of compounds of high interest represented by Formula VI:

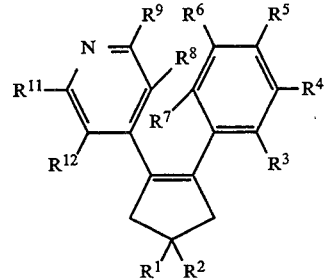

wherein each of $R^1$ and $R^2$ is independently selected from alkyl, hydrido, hydroxyalkyl, halo, haloalkyl, alkylcarboxyl and carboxyl; wherein $R^5$ is alkylsulfonyl or sulfamyl; wherein each of $R^3$, $R^4$, $R^6$, $R^7$, $R^8$, $R^9$, $R^{11}$ and $R^{12}$ is independently selected from hydrido, halo, alkyl, cyano and haloalkyl; or a pharmaceutically-acceptable salt thereof.

A preferred class of compounds consists of those compounds of Formula VI wherein $R^1$ and $R^2$ are identical radicals selected from alkyl, hydrido, hydroalkyl, halo, haloalkyl, alkylcarboxyl and carboxyl; wherein $R^3$, $R^4$, and $R^6$ through $R^{12}$ are hydrido; and wherein $R^5$ is alkylsulfonyl or sulfamyl; or a pharmaceutically-acceptable salt thereof.

A class of compounds of particular interest consists of those compounds of Formula VI wherein $R^1$ and $R^2$ are identical radicals selected from methyl, ethyl, hydroxymethyl, carbomethoxy, fluoro, trifluoromethyl and fluoromethyl; wherein each of $R^3$, $R^4$, and $R^6$ through $R^{12}$ is hydrido; and wherein $R^5$ is methylsulfonyl or sulfamyl; or a pharmaceutically-acceptable salt thereof.

A family of specific compounds of particular interest within Formula VI consists of compounds and pharmaceutically-acceptable salts thereof as follows:
4-[2-[4-(methylsulfonyl)phenyl]cyclopenten-1-yl]pyridine;
4-[2-(4-pyridinyl)cyclopenten-1-yl]benzenesulfonamide;
4-[2-[4-(methylsulfonyl)phenyl]-4,4-dimethylcyclopenten-1-yl]pyridine;
4-[2-[4-(methylsulfonyl)phenyl]-4,4-diethylcyclopenten-1-yl]pyridine;
4-[2-[4-(methylsulfonyl)phenyl]-4,4-di(hydroxymethyl)cyclopenten-1-yl]pyridine;
4-[2-[4-(methylsulfonyl)phenyl]-4,4-dicarbomethoxycyclopenten-1-yl]pyridine;
4-[2-[4-(methylsulfonyl)phenyl]-4,4-difluorocyclopenten-1-yl]pyridine;
4-[2-[4-(methylsulfonyl)phenyl]-4,4-di(trifluoromethyl)cyclopenten-1-yl]pyridine;
4-[2-[4-(methylsulfonyl)phenyl]-4,4-di(fluoromethyl)cyclopenten-1-yl]pyridine;
4-[2-[4-(pyridinyl)phenyl]-4,4-dimethylcyclopenten-1-yl]benzenesulfonamide;
4-[2-[4-(pyridinyl)phenyl]-4,4-diethylcyclopenten-1-yl]benzenesulfonamide;
4-[2-[4-(pyridinyl)phenyl]-4,4-di(hydroxymethyl)cyclopenten-1-yl]benzenesulfonamide;
4-[2-[4-(pyridinyl)phenyl]-4,4-dicarbomethoxycyclopenten-1-yl]benzenesulfonamide;
4-[2-[4-(pyridinyl)phenyl]-4,4-difluorocyclopenten-1-yl]benzenesulfonamide;
4-[2-[4-(pyridinyl)phenyl]-4,4-di(trifluoromethyl)cyclopenten-1-yl]benzenesulfonamide; and 4-[2-[4-(pyridinyl)phenyl]-4,4-di(fluoromethyl)cyclopenten-1-yl]benzenesulfonamide.

Where the term "alkyl" is used, either alone or within other terms such as "haloalkyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo and polyhaloalkyl radicals may have two or more of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about ten carbon atoms attached to a divalent sulfur atom, such as a methylthio radical. The term "aryl" embraces aromatic radicals such as phenyl, naphthyl and biphenyl. Preferred aryl radicals are those consisting of one, two, or three benzene rings. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. The terms "sulfamyl" or "sulfonamidyl" denotes a sulfonyl radical substituted with an amine radical, forming a sulfonamide (—SO$_2$NH$_2$). The term "carboxyl", whether used alone or with other terms, denotes —CO$_2$H. The term "alkylcarboxyl" means a radical containing an alkyl radical, as defined above, attached via a carbon atom to a "carboxyl" radical as defined above. Examples of such "alkylcarboxyl" radicals include (CH$_3$)$_3$CO$_2$C— and —CO$_2$CH$_3$.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are isomeric forms including diastereoisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–XIV, wherein the R$^1$–R$^{12}$ substituents are as defined for Formula I, above, except where further noted.

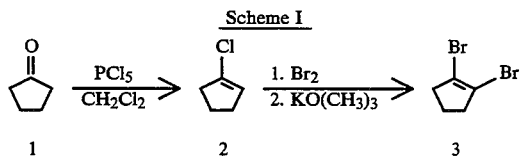

Scheme I

Synthetic Scheme I shows the preparation of 1,2-dibromocyclopentene (3) in two steps from commercially available cyclopentanone (1) using a procedure similar to the one developed by Montgomery, et al., [J. Am. Chem. Soc., 87, 1917 (1965)]. In step one, chlorination with phosphorus pentachloride gives 1-chlorocyclopentene (2). In step two, bromination of 2, followed by the elimination of hydrogen chloride on treatment with potassium tert-butoxide, provides 3.

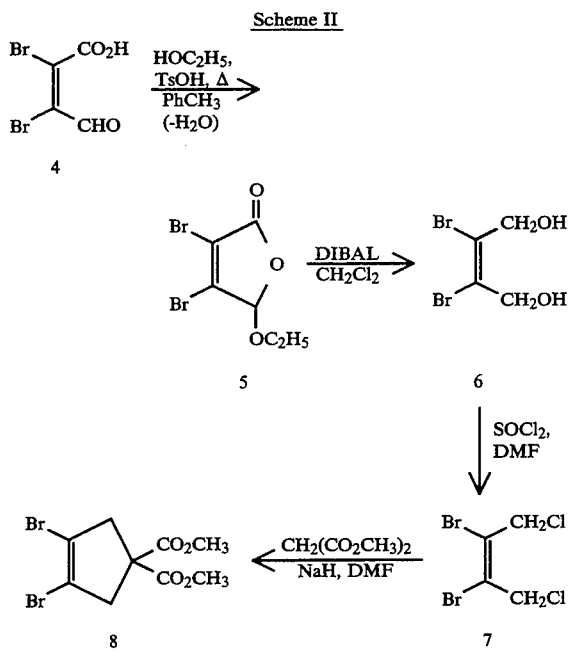

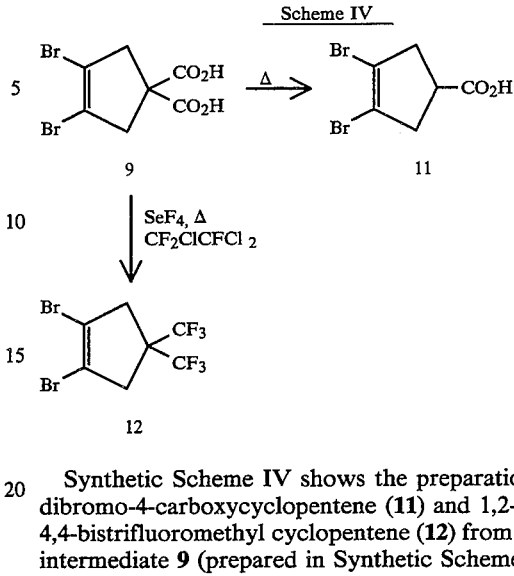

Synthetic Scheme II shows the preparation of 1,2-dibromo-4,4-dicarbomethoxycyclopentene (8) in four steps from commercially available mucobromic acid (4) using a procedure similar to the one developed by Lerstrub, et al., [*Syn. Metals*, 19, 647 (1987)]. In step one, mucobromic acid is converted to its ethyl ester 5 on treatment with ethanol in toluene at reflux in the presence of p-toluenesulfonic acid (TsOH). In step two, reduction of 5 with diisobutylaluminum hydride (DIBAL) in methylene chloride gives the diol 6. In step three, the diol 6 is reacted with thionyl chloride in dimethylformamide (DMF) to give the corresponding dichloride 7. In step four, the dichloride 7 is dialkylated with the dianion of methyl malonate to give 8.

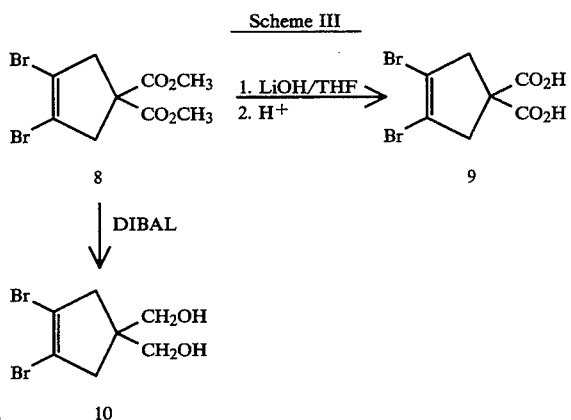

Synthetic Scheme III shows the preparation of 1,2-dibromo-4,4-dicarboxycyclopentene (9) and 1,2-bromo-4,4-di(hydroxymethyl)cyclopentene (10) from synthetic intermediate 8 (prepared in Synthetic Scheme II). Reaction of 8 with lithium hydroxide in tetrahydrofuran (THF) followed by careful acidification at 0° C. give the diacid 9; treatment with DIBAL gives the corresponding diol 10.

Synthetic Scheme IV shows the preparation of 1,2-dibromo-4-carboxycyclopentene (11) and 1,2-dibromo-4,4-bistrifluoromethyl cyclopentene (12) from synthetic intermediate 9 (prepared in Synthetic Scheme III). On heating, the diacid 9 is converted to the monoacid 10; treatment with selenium tetrafluoride in 1,1,2-trichlorotrifluoroethane at reflux gives the bistrifluoromethyl analog 12.

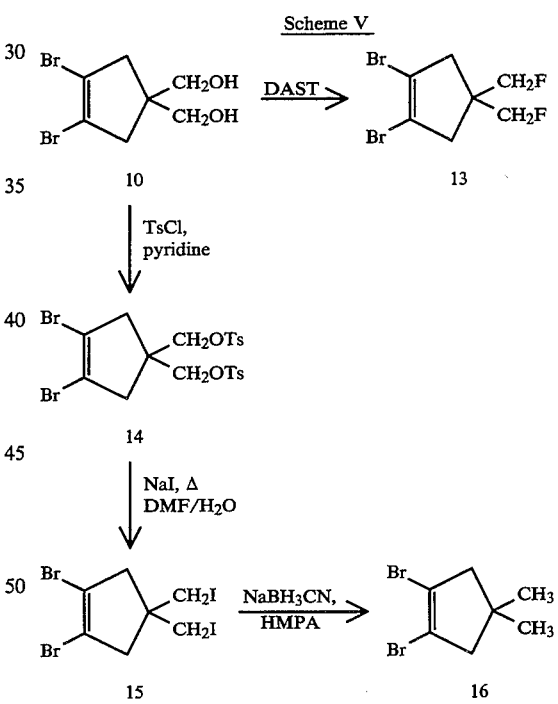

Synthetic Scheme V shows the preparation of 1,2-dibromo-4,4-di(fluoromethyl)cyclopentene (13) and 1,2-dibromo-4,4-dimethyl cyclopentene (16) from synthetic intermediate 10 (prepared in Synthetic Scheme III). Treatment of the diol 10 with diethylaminosulfurtrifluoride (DAST) in methylene chloride gives the corresponding fluoromethyl analog 13. Reaction of 10 with p-toluenesulfonyl chloride (TsCl) in the presence of pyridine gives the ditosylate 14. Reaction of 14 with sodium iodide in DMF/water (3:1) at 150° C. gives the di(iodomethyl) analog 15 which is subsequently reduced with sodium cyanoborohydride to give the dimethyl analog 16.

Scheme VI trichlorotrifluoroethane at reflux gives the 4,4-difluoro analog 19.

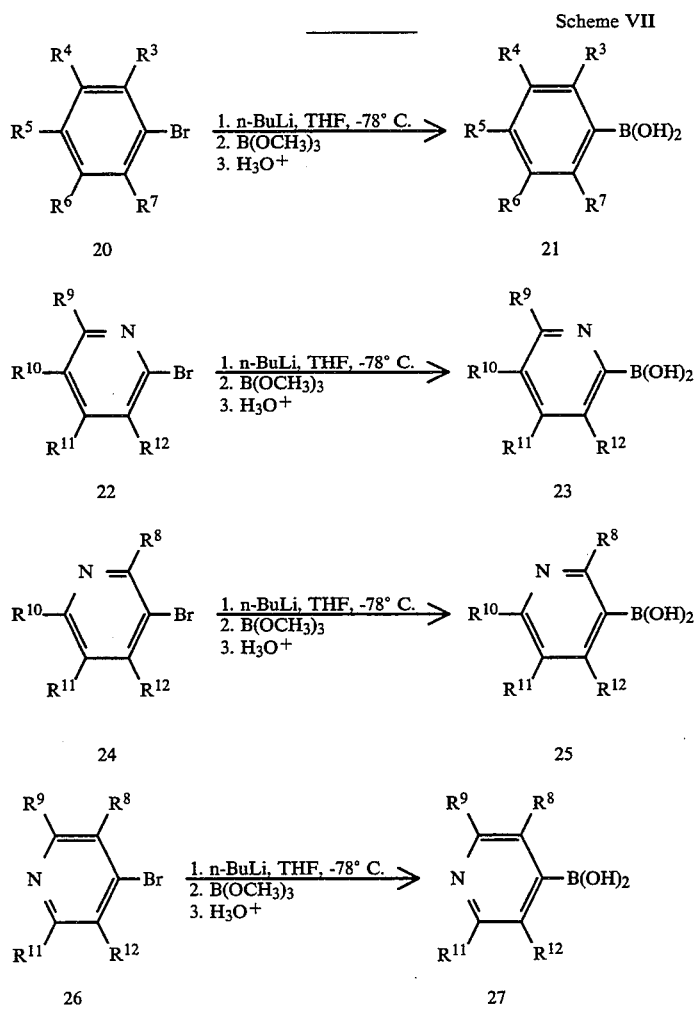

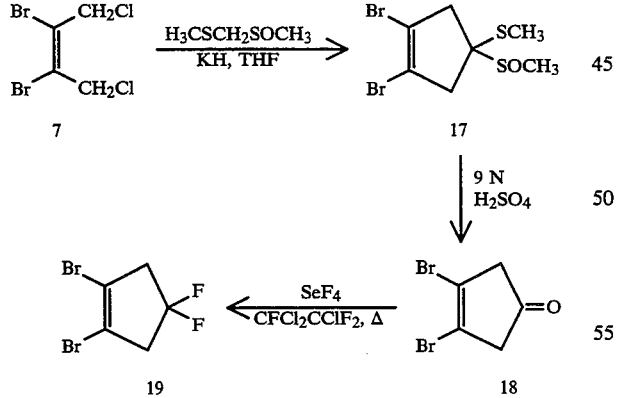

Synthetic Scheme VI shows the preparation of 1,2-dibromo-4,4-difluorocyclopentene (19) from synthetic intermediate 7 (prepared in Synthetic Scheme II). Using a procedure similar to the one developed by Ogura, et al., [*Tetrahedron Lett.*, 32, 2767 (1975)], the dianion of methyl methylthiomethyl sulfoxide (generated by potassium hydride in THF) is reacted with 7 to give the dimethyl dithioacetal S-oxide 17. Subsequent hydrolysis with 9 N sulfuric acid gives the corresponding ketone 18. Reaction of 18 with selenium tetrafluoride in 1,1,2-

Synthetic Scheme VII shows the preparation of the prerequisite substituted phenylboronic acids 21 and substituted pyridinylboronic acids 23, 25, and 27 from the available bromides 20, 22, 24, and 26, respectively. Halogen-metal interchange in THF at −78° C. generates the corresponding organolithium reagents which are reacted with trimethyl borate. Hydrolysis with 3 N hydrochloric acid provides the substituted phenylboronic acids 21 and the substituted pyridinylboronic acids 23, 25, and 27, respectively.

Scheme VIII

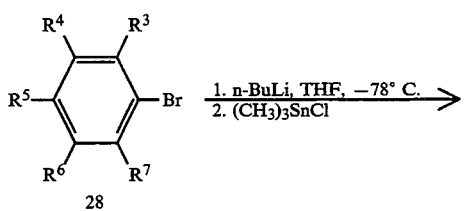

Scheme VIII -continued

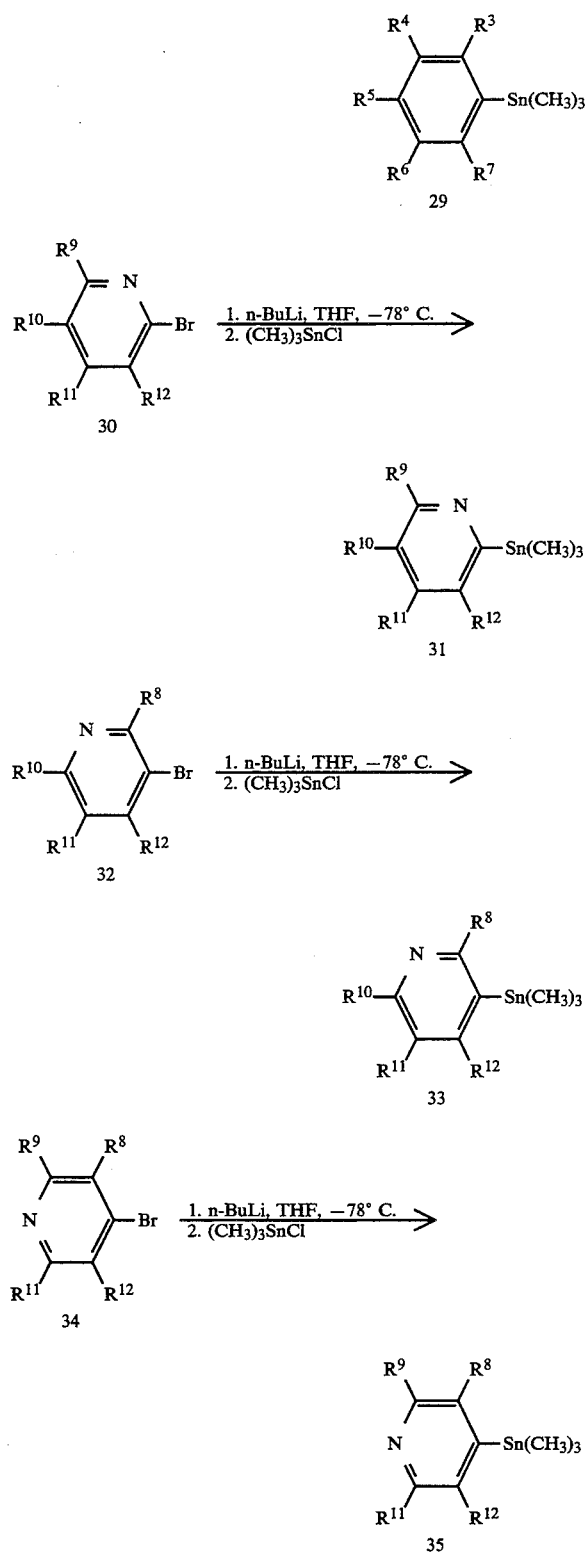

Synthetic Scheme VIII shows the preparation of the prerequisite substituted phenyltrimethyltin analogs 29 and substitutedpyridinyltrimethyltin analogs 31, 33, and 35 from the available bromides 28, 30, 32, and 34, respectively. Halogen-metal interchange in THF at −78° C. generates the organolithium reagents which are reacted with trimethyltin chloride. Purification provides the substitutedphenyltrimethyltin analogs 29 and the substitutedpyridinyltrimethyltin analogs 31, 33, and 35, respectively.

Scheme IX

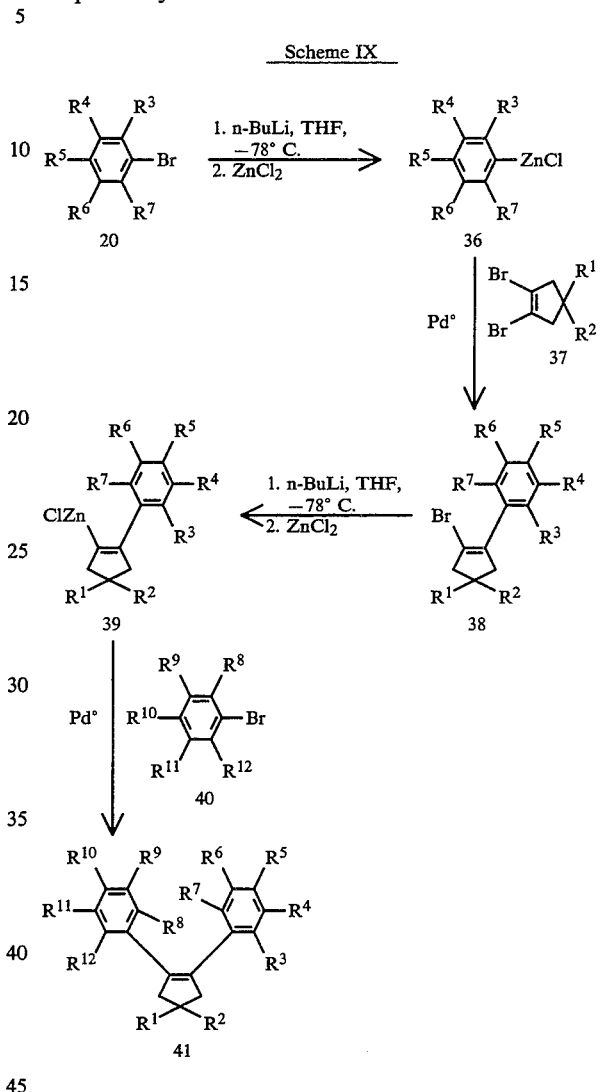

Synthetic Scheme IX shows the four step procedure for the preparation of 1,2-diaryl-4,4-disubstitutedcyclopentene anti-inflammatory agents 41 from the available bromides 20 using a sequential coupling procedure which is similar to the coupling procedure developed by Negishi, et al., [*J. Org. Chem.*, 42, 1821 (1977)]. In step one, halogen-metal interchange of 20 with n-butyl lithium in THF at −78° C. gives the corresponding organolithium reagents which subsequently react with zinc chloride to give the organozinc reagents 36. In step two, the organozinc reagents 36 are coupled with the 1,2-dibromo-4,4-disubstitutedcyclopentenes 37 (prepared in Synthetic Schemes I-IV) in the presence of a Pd° catalyst, e.g., tetrakis(triphenylphosphine)palladium (0), to give the monocoupled bromides 38 (after separation from the biscoupled by-product). In step three, the bromides 38 are treated as above to give the organozinc reagents 39. In step four, the monocoupled organozinc reagents 39 are coupled with the arylbromides 40 (which can be identical with 20 when $R^3=R^8$, $R^4=R^9$, $R^5=R^{10}$, $R^6=R^{11}$, and $R^7=R^{12}$) to give the 1 2-diaryl-4 4-disubstitutedcyclopentene anti-inflammatory agents 41 of this invention.

Scheme X

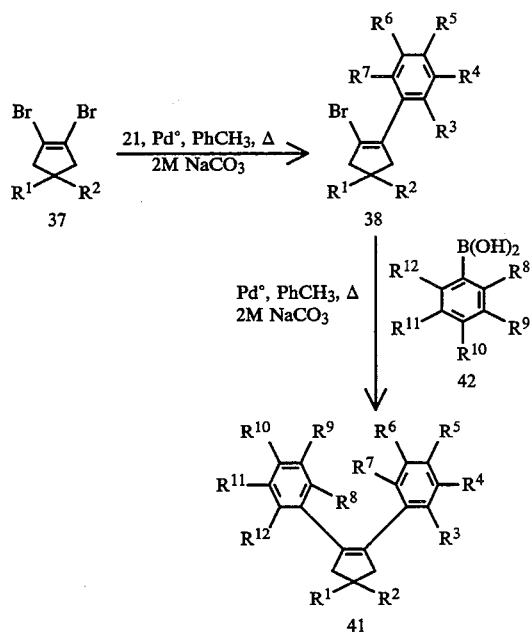

Scheme XI

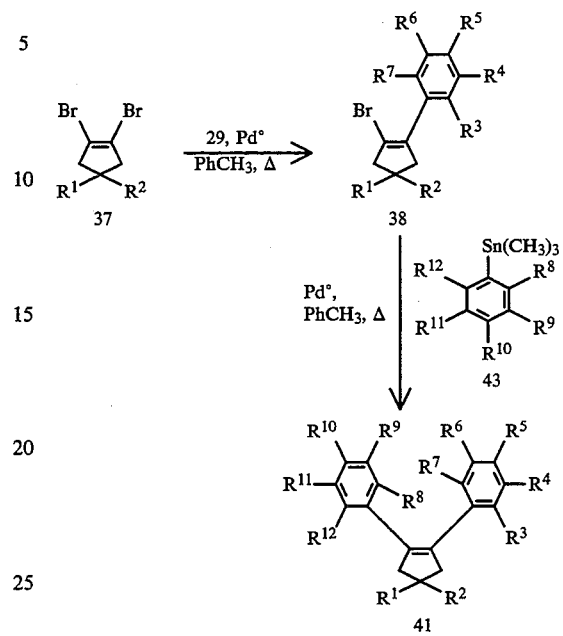

Synthetic Scheme X shows the two step procedure for the preparation of 1,2-diaryl-4,4-disubstitutedcyclopentene anti-inflammatory agents 41 from 1,2-dibromo-4,4-disubstitutedcyclopentenes 37 (prepared in Synthetic Scheme I–VI) and substituted phenylboronic acids 21 and 42 (prepared in Synthetic Scheme VII) using a sequential coupling procedure which is similar to the coupling procedure developed by Suzuki, et al., [*Syn. Commun.*, 11, 513 (1981)]. In step one, the dibromides 37 are treated with the boronic acids 21 in toluene at reflux in the presence of Pd° catalyst, e.g., tetrakis(triphenylphosphine)palladium (0), and 2M sodium carbonate to give the monocoupled bromides 38 (after separation from the biscoupled by-product). In step two, the monocoupled bromides 38 are coupled as above with the boronic acids 42 (which can be identical with 21 when $R^3=R^8$, $R^4=R^9$, $R^5=R^{10}$, $R^6=R^{11}$, and $R^7=R^{12}$) give the 1,2-diaryl-4,4-disubstitutedcyclopentene anti-inflammatory agents 41 of this invention.

Synthetic Scheme XI shows the two step procedure for the preparation of 1,2-diaryl-4,4-disubstitutedcyclopentene anti-inflammatory agents 41 from 1,2-dibromo-4,4-disubstitutedcyclopentenes 37 (prepared in Synthetic Scheme I–IV) and substitutedphenyltrimethyltin analogs 29 and 43 (prepared in Synthetic Scheme VII) using a sequential coupling procedure which is similar to the coupling procedure developed by Stille, et al., [*J. Am. Chem. Soc.*, 101, 4992 (1979))]. In step one, the dibromides 37 are treated with the trimethyltin analogs 29 in toluene at reflux in the presence of a Pd° catalyst, e.g., tetrakis(triphenylphosphine)palladium (0), and 2M sodium carbonate to give the monocoupled bromides 38 (after separation from the biscoupled by-product). In step two, the monocoupled bromides 38 are coupled as above with the trimethyltin analogs 43 (which can be identical with 29 when $R^3=R^8$, $R^4=R^9$, $R^5=R^{10}$, $R^6=R^{11}$, and $R^7=R^{12}$) to give the 1,2-diaryl-4,4-disubstitutedcyclopentene anti-inflammatory agents 41 of this invention.

Scheme XII

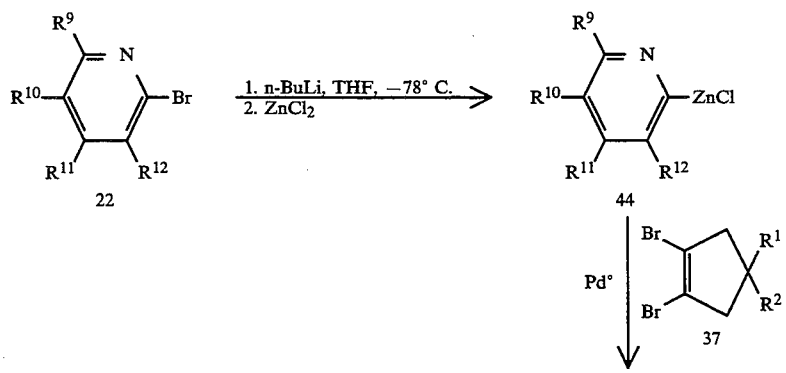

Scheme XII

-continued

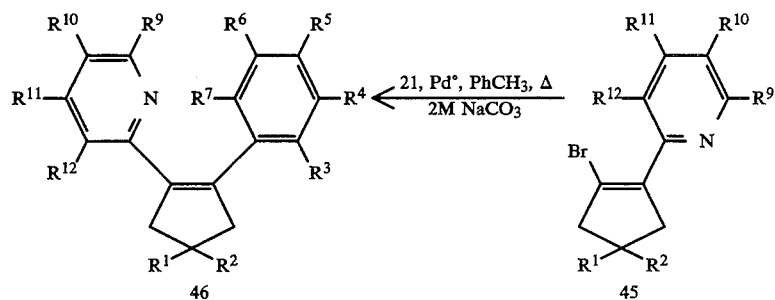

Synthetic Scheme XII shows the three step preparation of 1-aryl-2-(2-pyridinyl)-4,4-disubstitutedcyclopentene anti-inflammatory agents 46 from 1,2-dibromo-4,4-disubstitutedcyclopentenes 37 (prepared in Synthetic Scheme (I–IV) and the available 2-bromopyridines 22. In step one, halogen-metal interchange of 22 with n-butyl lithium in THF at −78° C. gives the 2-lithiopyridines which subsequently react with zinc chloride to give the corresponding 2-pyridinylzinc reagents 44. In step two, a Negishi coupling (see Synthetic Scheme IX) of the 2-pyridinylzinc reagents 44 with 37 gives the monocoupled 2-pyridinyl bromides 45 (after separation from the biscoupled by-product). In step three, a Suzuki coupling (see Synthetic Scheme X) of the monocoupled 2-pyridinyl bromides 45 with substituted phenylboronic acids 21 (prepared in Synthetic Scheme VII) gives the 1-aryl-2-(2-pyridinyl)-4,4-disubstitutedcyclopentene anti-inflammatory agents 46 of this invention.

Synthetic Scheme XIII shows the three step preparation of 1-aryl-2-(3-pyridinyl)4,4-disubstitutedcyclopentene anti-inflammatory agents 49 from 1,2-dibromo-4,4-disubstitutedcyclopentenes 37 (prepared in Synthetic Scheme I–IV) and the available 3-bromopyridines 24. In step one, halogen-metal interchange of 24 with n-butyl lithium in THF at 78° C. gives the 3-lithiopyridines which subsequently react with zinc chloride to give the corresponding 3-pyridinylzinc reagents 47. In step two, a Negishi coupling ((see Synthetic Scheme IX) of the 3-pyridinyl bromides 48 (after separation from the biscoupled by-product). In step three, a Suzuki coupling (see Synthetic Scheme X) of the monocoupled 3-pyridinyl bromides 48 with substituted phenylnboronic acid 21 (prepared in Synthetic Scheme VII) gives the 1-aryl-2-(3-pyridinyl)- 4,4-disubstitutedcyclopentene anti-inflammatory agents 49 of this invention.

Scheme XIII

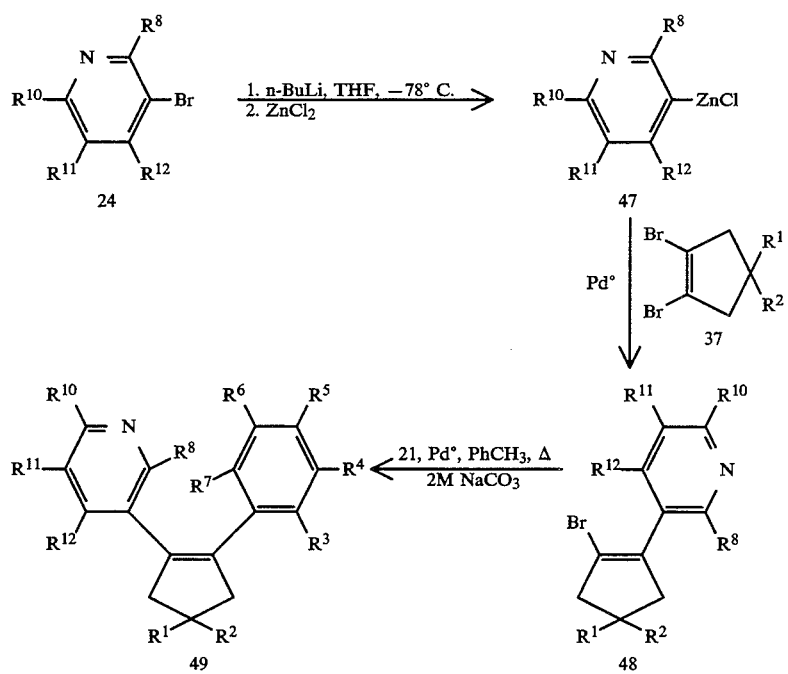

Scheme XIV

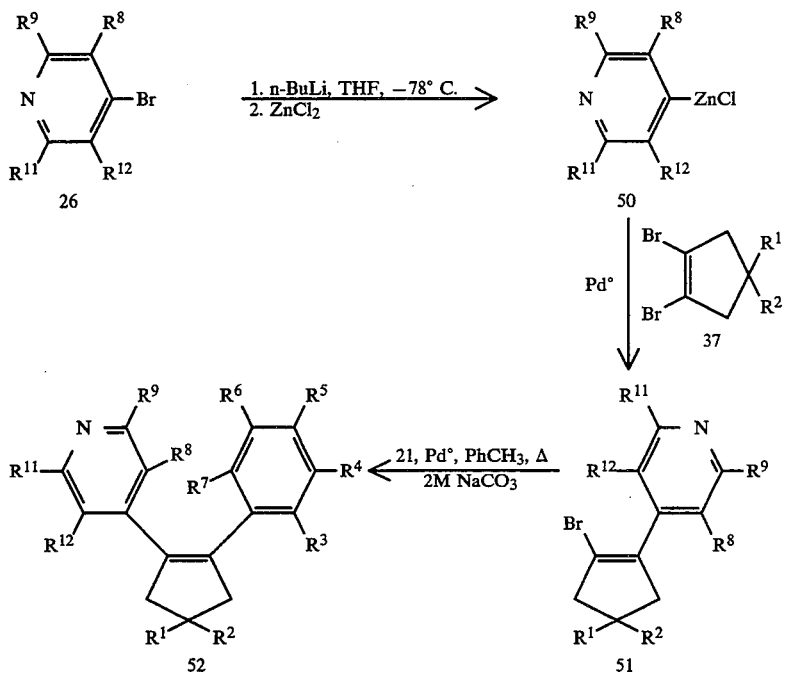

Synthetic Scheme XIV shows the three step preparation of 1-aryl-2-(4-pyridinyl)-4,4-disubstitutedcyclopentene anti-inflammatory agents 52 from 1,2-dibromo-4,4-disubstitutedcyclopentenes 37 (prepared in Synthetic Scheme I–IV) and the available 4-bromopyridines 26. In step one, halogen-metal interchange of 26 with n-butyl lithium in THF at −78° C. gives the 4-lithiopyridines which subsequently react with zinc chloride to give the corresponding 4-pyridinylzinc reagents 50. In step two, a Negishi coupling (see Synthetic Scheme IX) of the 4-pyridinylzinc reagents 50 with 37 gives the monocoupled 4-pyridinyl bromides 51 (after separation from the biscoupled by-product). In step three, a Suzuki coupling (see Synthetic X) of the monocoupled 4-pyridinyl bromides 51 with substituted phenylboronic acids 21 (prepared in Synthetic Scheme VII) gives the 1-aryl-2-(4-pyridinyl)-4,4-disubstitutedcyclopentene anti-inflammatory agents 52 of this invention.

The following examples contain detailed descriptions of the methods of preparation of compounds of Formula I–VI. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

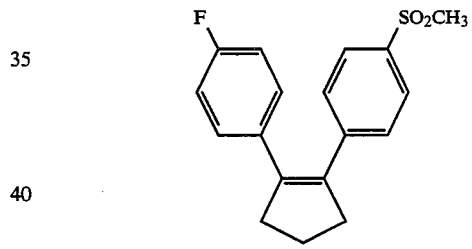

1-[2-(4-fluorophenyl)cyclopenten-1-yl]-
4-(methylsulfonyl)benzene

Step 1: Preparation of 4-Methylthiophenylboronic Acid

Under nitrogen, a stirred solution of 30 g (150 mmol) of 4-bromothioanisole (Aldrich) in 1500 mL of anhydrous THF at −78° C. was treated with 180 mmol of n-butyllithium in hexane. After 30 minutes, 51 mL (450 mmol) of trimethylborate was added neat and the reaction was allowed to warm to ambient temperature overnight. A solution of 300 mL of 10% NaOH was added and the mixture stirred vigorously for 1 h. The solvent was removed in vacuo, the pH adjusted to 4–5, and the product collected by filtration. Repeated washings with hexane and water provided 21 g (83%) of 4-methylthiophenylboronic acid (21 in Synthetic Scheme VII when $R^5=SCH_3$ and $R^3$, $R^4$, $R^6$, and $R^7=H$) as a colorless solid: NMR (DMSO-$d_6$) d 2.47 (s, 3H), 7.20 (d, J=8 Hz, 2H), 7.71 (d, J=8 Hz, 2H), 7.96 (br s, 2H).

Step 2: Preparation of
1-(2-Bromocyclomenten-1-yl)-4-(Methylthio)Benzene

Under nitrogen, 36.4 g (161 mmol) of 1,2-dibromocyclopentene (Aldrich) was reacted with 18.0 g (107 mmol) of 4-methylthiophenylboronic acid (Step 1) in 550 mL of toluene, 365 mL of ethanol, and 235 mL of 2M Na$_2$CO$_3$ in the presence of 6.0 g (5 mol %) of Pd(PPh$_3$)$_4$. The reaction was vigorously stirred at reflux overnight and concentrated in vacuo. The residue was dissolved in ethyl acetate and washed with water, dried (MgSO$_4$), and reconcentrated. Purification by silica gel chromatography (Waters Prep-500) with hexane gave 9.39 g (22%) of 1-(2-bromocyclopenten-1-yl)-4-(methylthio)benzene (38 in Synthetic Scheme X when R$^5$=SCH$_3$ and R$^1$, R$^2$, R$^3$, R$^4$, R$^6$, and R$^7$=H) as a solid: mp 52°–54° C.; NMR (CDCl$_3$) d 1.98–2.09 (m, 2H), 2.50 (s, 3H), 2.70–2.78 (m, 2H), 2.80–2.89 (m, 2H), 7.24 (d, J=8 Hz, 2H), 7.55 (d, J=8 Hz, 2H).

Step 3: Preparation of 1-[2-(4-Fluorophenyl)Cyclopenten-1-yl]-4-(Methylthio)Benzene Under nitrogen, 1.5 g (5.6 mmol) of 1-(2-bromocyclopenten-1-yl)-4-(methylthio)benzene (Step 2) was reacted with 1.5 g (11 mmol) of 4-fluorophenylboronic acid (Lancaster) in 30 mL of toluene, 20 mL of ethanol, and 25 mL of 2M Na$_2$CO$_3$ in the presence of 250 mg of Pd(PPh$_3$)$_4$. The reaction was vigorously stirred at reflux overnight and concentrated in vacuo. The residue was dissolved in ethyl acetate and washed with water, dried (MgSO$_4$), and reconcentrated. Purification by silica gel chromatography with hexane gave 1-[2-(4-fluorophenyl) cyclopenten-1-yl]-4-(methylthio)benzene (41 in Synthetic Scheme X when R$^5$=SCH$_3$, R$^{10}$=F, and R$^1$, R$^2$, R$^3$, R$^4$, R$^6$, R$^7$, R$^8$, R$^9$, R$^{11}$, and R$^{12}$=H) as a colorless solid. mp 46°–47° C.; NMR (CDCl$_3$) d 2.04 (m, J=7 Hz, 2H), 2.45 (s, 3H), 2.86, (t, J=7 Hz, 4H), 6.86–6.94 (m, 2H), 7.08 (br s, 4H), 7.10–7.18 (m, 2H).

Step 4: Preparation of 1-[2-(4-Fluorophenyl)Cyclopenten-1-yl]-4-(Methylsulfonyl)Benzene A solution of 1.5 g (5. mmol) of 1-[2-(4-fluorophenyl) cyclopenten-1-yl]-4-(methylthio)benzene (Step 3) in 46 mL of methanol/thf (1:1) was slowly treated with 5.2 g (8.4 mmol) of Oxone ® [2 KHSO$_5$.K$_2$SO$_4$] in 23 mL of water. After stirring for 4 h, the solvent was removed in vacuo. The residue was dissolved in ethyl acetate and washed with water and brine, dried (MgSO$_4$), and reconcentrated. Recrystallization from ethyl acetate/hexane provided 960 mg (54%) of 1-[2-(4-fluorophenyl) cyclopenten-1-yl]-4- (methylsulfonyl)benzene (41 in Synthetic Scheme X when R$^5$=SO$_2$CH$_3$, R$^{10}$=F, and R$^1$, R$^2$, R$^3$, R$^4$, R$^6$, R$^7$, R$^8$, R$^9$, R$^{11}$, and R$^{12}$=H) as a colorless solid: mp 138°–139° C.; NMR (CDCl$_3$) d 2.09 (m, J=7 Hz, 2H), 2.91 (t, J=7 Hz, 4H), 3.04 (s, 3H), 6.88–6.96 (m, 2H), 7.06–7.14 (m, 2H), 7.32 (d, J=8 Hz, 2 H), 7.76 (d, J=8 Hz, 2H). MS (EI) m/e (rel intensity) 316 (100), 237 (41), 161 (13); HRMS. Calc'd for C$_{18}$H$_{17}$FO$_2$S: 316.0933. Found: 316.0943. Anal. Calc'd for C$_{18}$H$_{17}$FO$_2$S: C, 68.33; H, 5.42; F, 6.00; S, 10.13. Found: C, 68.08; H, 5.45; F, 6.42; S, 9.98.

EXAMPLE 2

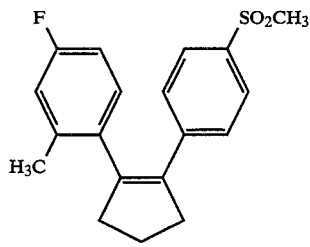

1-[2-(4-fluoro-2-methylphenyl)cyclopenten-1-yl]-4-(methylsulfonyl)benzene

Step 1: Preparation of 4-Fluoro-2-Methylphenylboronic Acid

Following the synthetic procedure outlined in Step 1 of Example 1, 2-bromo-5-fluorotoluene (Aldrich) was converted to 4-fluoro-2-methylphenylboronic acid: NMR (DMSO-d$_6$) d 2.40 (s, 3H), 6.85–6.99 (m, 2H), 7.46 (d, J=7 Hz, 1H).

Step 2: Preparation of 1-[2-(4-Fluoro-2-Methylphenyl)Cyclopenten-1-yl]-4-(Methylthio)Benzene Following the synthetic procedure outlined in Step 3 of Example 1, 500 mg (1.9 mmol) of 1-(2-bromocyclopenten-1-yl)-4-(methylthio) benzene (Example 1, Step 2) was reacted with 590 mg (3.8 mmol) of 4-fluoro-2-methylphenylboronic acid (Step 1). Purification by silica gel chromatography (MPLC) with hexane gave 500 mg (95%) of 1-[2-(4-fluoro-2-methylphenyl) cyclopenten-1-yl]-4-(methylthio)benzene as a colorless solid: mp 67°–68° C.; NMR (CDCl$_3$) d 2.00–2.11 (m, 2H), 2.05 (s, 3H), 2.41 (s, 3H), 2.69–2.77 (m, 2H), 2.86–2.95 (m, 2H), 6.80–7.07 (m, 7H).

Step 3: Preparation of 1-[2-(4-Fluoro-2-Methylphenyl) Cyclopenten-1-yl]-4-(Methylsulfonyl)Benzene.

Following the synthetic procedure outlined in Step 4 of Example 1, 470 mg (1.6 mmol) of 1-[2-(4-fluoro-2-methylphenyl) cyclopenten-1-yl]-4-(methylthio)benzene (Step 2) was oxidized. Purification by silica gel chromatography with hexane/ethyl acetate (1:4) and subsequent recrystallization from ethyl acetate/hexane gave 1-[2-(4-fluoro-2-methylphenyl)cyclopenten-1-yl]-4-(methylsulfonyl)benzene as a colorless solid: mp 112.5°–113.5° C.; NMR (CDCl$_3$) d 2.03–2.16 (m, 2H), 2.05 (s, 3H), 2.74–2.82 (m, 2H), 2.91–3.01 (m, 2H), 2.98 (s, 3H), 6.83–6.93 (m, 2H), 6.97–7.04 (m, 1H), 7.19 (d, J=8 Hz, 2H), 7.68 (d, J=8 Hz, 2H); MS (FAB) m/e (rel intensity) 337 (100), 331 (46); HRMS. Calc'd for C$_{19}$H$_{19}$FO$_2$S: 330.1090. Found: 330.1096. Anal. Calc'd for C$_{19}$H$_{19}$FO$_2$S: C, 69.07; H, 5.80; F, 5.75; S, 9.70. Found: C, 69.37; H, 5.81; F, 5.40; S, 9.78.

EXAMPLE 3

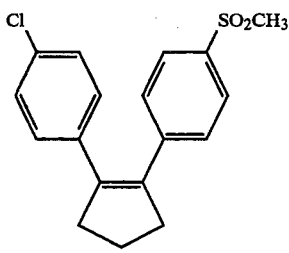

1-[2-(4-chlorophenyl)cyclopenten-1-yl]-
4-(methylsulfonyl)benzene

Step 1: Preparation of 1-[2-(4-Chlorophenyl)Cyclopenten-1-yl]-4-(Methylthio)Benzene Following the synthetic procedure outlined in Step 3 of Example 1, 250 mg (0.93 mmol) of 1-(2-bromocyclopenten-1-yl)-4-(methylthio)benzene (Example 1, Step 2) was reacted with 300 mg (1.9 mmol) of 4-chlorophenylboronic acid (Lancaster). Purification by silica gel chromatography (MPLC) with hexane gave 290 mg of 1-[2-(4-chlorophenyl) cyclopenten-1-yl]-4-(methylthio)benzene as a colorless solid: mp 72°-74° C.; NMR (CDCl$_3$) d 2.04 (m, J=7 Hz, 2H), 2.46 (s, 3H), 2.86 (t, J=7 Hz, 4H), 7.07-7.21 (m, 8H).

Step 2: Preparation of 1-[2-(4-Chlorophenyl)Cyclopenten-1-yl]-4-(Methylsulfonyl)-Benzene Following the synthetic procedure outlined in Step 4 of Example 1, 280 mg (0.93 mmol) of 1-[2-(4-chlorophenyl)cyclopenten-1-yl]-4- (methylthio)benzene (Step 1) was oxidized. Purification by silica gel chromatography (MPLC) with hexane and subsequent recrystallization from ethyl acetate/hexane gave 192 mg (62%) of 1-[2-(4-chlorophenyl)cyclopenten-1-yl]-4-(methylsulfonyl)benzene as a colorless solid: mp 127.5°-128.5° C.; NMR (CDCl$_3$) d 2.09 (m, J=7 Hz, 2H), 2.91 (t, J=7 Hz, 4H), 3.04 (s, 3H), 7.06, (d, J=8 Hz, 2H). 7.21 (d, J=8 Hz, 2H), 7.32 (d, J=8 Hz, 2H), 7.77 (d, J=8 Hz, 2H); MS (EI) m/e (rel intensity) 332 (100), 297 (6), 218 (30); HRMS. Calc'd for C$_{18}$H$_{17}$ClO$_2$S: 332.0638. Found: 332.0628. Anal. Calc'd for C$_{18}$H$_{17}$ClO$_2$S: C, 64.95; H, 5.15; Cl, 10.65; S, 9.63. Found: C, 64.97; H, 5.15; Cl, 10.50; S, 9.58.

EXAMPLE 4

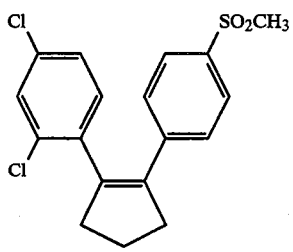

1-[2-(2,4-dichlorophenyl)cyclopenten-1-yl]-
4-(methylsulfonyl)benzene

Step 1: Preparation of 1-[2-(2,4-Dichlorophenyl)Cyclopenten-1-yl]-4-(Methylsulfonyl)Benzene Following the synthetic procedure outlined in Step 3 of Example 1, 280 mg (0.93 mmol) of 1-(2-bromocyclopenten-1-yl)-4-(methylthio)benzene (Example 1, Step 2) was reacted with 350 mg (1.9 mmol) of 2,4-dichlorophenylboronic acid (Lancaster). Purification by silica gel chromatography (MPLC) with hexane gave 280 mg of 1-[2-(2,4-dichlorophenyl)cyclopenten-1-yl]-4-(methylthio)benzene as an oil: NMR (CDCl$_3$) d 2.10 (m, J=7 Hz, 2H), 2.41 (s, 3H), 2.81 (t, J=8 Hz, 4H), 2.92 (m, J=8 Hz, 2H), 6.95-7.21 (m, 6H), 7.40 (s, 1H).

Step 2: Preparation of 1-[2-(2,4-Dichlorophenyl)Cyclopenten-1-yl]-4-(Methylsulfonyl)Benzene Following the synthetic procedure outlined in Step 4 of Example 1, 280 mg (0.85 mmol) of 1-[2-(4-chlorophenyl)cyclopenten-1-yl]-4-(methylthio)benzene (Step 1) was oxidized. Purification by silica gel chromatography (MPLC) with hexane and subsequent lyophilization from acetonitrile/water (1:1) gave 158 mg (51%) of 1-[2-(2,4-dichlorophenyl) cyclopenten-1-yl]-4-(methylsulfonyl)benzene as a solid: NMR (CDCl$_3$) d 2 13 (m J=8 Hz 2H) 2.84 (t J=8 Hz 2H), 2.96 (t, J=8 Hz, 2H), 3.00 (s, 3H), 6.97 (d, J=8 Hz, 1H). 7.14-7.23 (m, 4H), 7.42 (d, J=2 Hz, 1H), 7.71 (d, J=9 Hz, 2H); MS (EI) m/e (rel intensity) 368 (61), 366 (91), 252 (100) 215 (64) 128 (47); HRMS Calc'd for C$_{18}$H$_{16}$Cl$_2$O$_2$S: 366 0242 Found: 332.0249. Anal. Calc'd for C$_{18}$H$_{16}$Cl$_2$O$_2$S: C, 58.86; H, 4.39; Cl, 19.37; S, 8.73. Found: C, 58.43; H, 4.47; Cl, 19.45; S, 8.82.

EXAMPLE 5

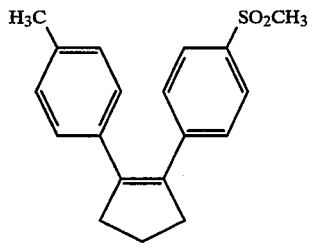

1-[2-(4-methylphenyl)cyclopenten-1-yl]-
4-(methylsulfonyl)benzene

Step 1: Preparation of 1-[2-(4-Methylphenyl)Cyclopenten-1-yl]-4-(Methylthio)Benzene Following the synthetic procedure outlined in Step 3 of Example 1, 250 mg (0.93 mmol) of 1-(2-bromocyclopenten-1-yl)-4-(methylthio)benzene (Example 1, Step 2) was reacted with 260 mg (1.9 mmol) of 4-methylphenylboronic acid (Lancaster). Purification by silica gel chromatography (MPLC) with hexane gave 240 mg (92%) of 1-[2-(4-methyl phenyl)cyclopenten-1-yl]-4-(methylthio)benzene as a colorless solid: mp 64.5°-66.5° C.; NMR (CDCl$_3$) d 2.03 (m, J=7 Hz, 2H), 2.30 (s, 3H), 2.45 (s, 3H), 2.86 (t, J=7 Hz, 4H), 6.99-7.15 (m, 8H).

Step 2: Preparation of 1-[2-(4-Methylphenyl)Cyclopenten-1-yl]-4-(Methylsulfonyl)Benzene Following the synthetic procedure outlined in Step 4 of Example 1, 210 mg ( 0.75 mmol) of 1-[2-(4-methylphenyl)cyclopenten-1-yl]-4-(methylthio)benzene (Step 1) was oxidized. Purification by silica gel chromatography (MPLC) with ethyl acetate/hexane (1:4) and subsequent recrystallization gave 140 mg (60%) of 1-[2-(4-methylphenyl) cyclopenten-1-yl]-4-(methylsulfonyl)-benzene as a colorless solid: mp 118.0°–118.5° C.; NMR (CDCl3) d 2.07 (m, J=7 Hz, 2H), 2.32 (s, 3H), 2.90 (t, J=7 Hz, 4H), 3.03 (s, 3H), 6.99–7.08 (m, 4H), 7.34 (d, J=8 Hz, 2H), 7.74 (d, J=8 Hz, 2H); MS (EI) m/e (rel intensity) 312 (100), 297 (10), 233 (11) 218 (22); HRMS. Calc'd for C19H20O2S: 312.1184. Found: 312.1194. Anal. Calc'd for C19H20O2S: C, 73.04; H, 6.45; S, 10.26. Found: C, 73.22; H, 6.65; S, 10.24.

EXAMPLE 6

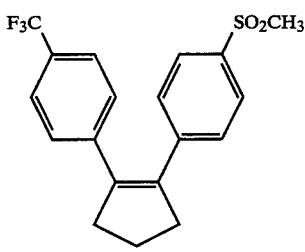

1-[2-(4-trifluoromethylphenyl)cyclopenten-1-yl]-4-(methylsulfonyl)benzene

Step 1: Preparation of 4-Trifluoromethylphenylboronic Acid

Following the synthetic procedure outlined in Step 1 of Example 1, 4-bromobenzotrifluoride (Aldrich) was converted to 4-trifluoromethyl phenylboronic acid: NMR (DMSO-d6) d 7.68 (d, J=8 Hz, 2H), 7.98 (d, J=8 Hz, 2H).

Step 2; Preparation of 1-[2-(4-Trifluoromethylphenyl)Cyclopenten-1-yl]-4-(Methylthio)Benzene Following the synthetic procedure outlined in Step 3 of Example 1, 240 mg (0.89 mmol) of 1-(2-bromocyclopenten-1-yl)-4-(methylthio) benzene (Example 1, Step 2) was reacted with 360 mg (1.8 mmol) of 4-trifluoromethylphenylboronic acid (Step 1). Purification by silica gel chromatography (MPLC) with hexane gave 240 mg (81%) of 1-[2-(4-trifluoromethylphenyl)cyclopenten-1-yl]-4-(methylthio)benzene as a colorless solid: mp 60.0°–61.5° C.; NMR (CDCl3) d 2.06 (m, J=7 Hz, 2H), 2.46 (s, 3H), 2.89 (t, J=7 Hz, 4H), 7.06 (d, J=6 Hz, 2H), 7.10 (d, J=6 Hz, 2H), 7.27 (d, J=8 Hz, 2H), 7.46 (d, J=8 Hz, 2H).

Step 3: Preparation of 1-[2-(4-Trifluoromethylphenyl)Cyclopenten-1-yl]-4-(Methylsulfonyl)Benzene Following the synthetic procedure outlined in Step 4 of Example 1, 215 mg (0.75 mmol) of 1-[2-(4-trifluoromethylphenyl)cyclopenten-1-yl]-4-(methylthio)-benzene (Step 2) was oxidized. Purification by silica gel chromatography (MPLC) with ethyl acetate/hexane (1:4) and subsequent recrystallization gave 163 mg (69%) of 1-[2-(4-trifluoromethylphenyl) cyclopenten-1-yl]-4-(methylsulfonyl)benzene as a colorless solid: mp 134.5°–135.0° C.; NMR (CDCl3) d 2.12 (m, J=7 Hz, 2H), 2.95 (t, J=7 Hz, 4H), 3.05 (s, 3H), 7.24 (d, J=8 Hz, 2H), 7.31 (d, J=8 Hz, 2H), 7.49 (d, J=8 Hz, 2H), 7.78 (d, J=8 Hz, 2H); MS (EI) m/e (rel intensity) 312 (100), 297 (10), 233 (11) 218 (22); HRMS. Calc'd for C19H20O2S: 312.1184. Found: 312.1194. Anal. Calc'd for C19H20O2S: C, 73.04; H, 6.45; S, 10.26. Found: C, 73.22; H, 6.65; S, 10.24.

EXAMPLE 7

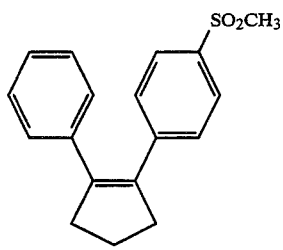

1-(2-phenylcyclopenten-1-yl)-4-(methylsulfonyl)benzene

Step 1: Preparation of 1-Bromo-2-Phenylcyclopentene

Following a synthetic procedure which was similar to the one outlined in Step 2 of Example 1, 4.40 g (19.4 mmol) of 1,2-dibromocyclopentene was reacted with 2.0 g (17.7 mmol) of phenylboronic acid (Aldrich). Purification by silica gel chromatography (Waters Prep-500) with hexane gave 1.61 g (42%) of 1-bromo-2-phenylcyclopentene as an oil: NMR (CDCl3) d 2.01–2.10 (m, 2H), 2.74–2.82 (m, 2H), 2.82–2.90 (m, 2H), 7.27–7.33 (m, 1H), 7.33–7.41 (m, 2H), 7.57–7.63 (m, 2H).

Step 2: Preparation of 1-(2-(Phenylcyclopenten-1-yl)-4-(Methylthio)Benzene

Following a synthetic procedure which was similar to the one outlined in Step 3 of Example 1, 750 mg (3.4 mmol) of 1-bromo-2-phenylcyclopentene (Step 1) was reacted with 1.2 g (6.8 mmol) of 4-methylthiophenylboronic acid (Example 1, Step 1). Purification by silica gel chromatography (MPLC) with hexane gave 800 mg (89%) of 1-(2-phenylcyclopenten-1-yl) -4-(methylthio)-benzene as an oil: NMR (CDCl3) d 2.00–2.17 (m, 2H), 2.46 (s, 3H), 2.86–3.01 (m, 4H), 7.08–7.19 (m, 4H), 7.19–7.32 (m, 5H).

Step 3: Preparation of 1-(2-(Phenylcyclopenten1yl)-4-(Methylsulfonyl)Benzene

Following the synthetic procedure outlined in Step 4 of Example 1, 800 mg (3.0 mmol) of 1-(2-phenylcyclopenten-1-yl)-4-(methylthio) benzene (Step 2) was oxidized. Purification by silica gel chromatography (MPLC) with hexane gave 300 mg (30%) of 1-(2-phenylcyclopenten-1-yl)-4-(methylsulfonyl) benzene as a colorless solid: mp 135.5°–137.0° C.; NMR (DMSO-d6) d 2.01 (m, J=7 Hz, 2H), 2.91 (t, J=7 Hz, 4H), 3.18 (s, 3H), 7.12–7.18 (m, 2H), 7.18–7.31 (m, 3H), 7.37 (d, J=8 Hz, 2H), 7.76 (d, J=8 Hz, 2H); MS (EI) m/e (rel intensity) 298 (100), 219 (30), 141 (30); HRMS Calc'd for C18H18O2S: 298.1028. Found: 298.1056. Anal. Calc'd for C18H18O2S: C, 72.45; H, 6.08; S, 10.74. Found: C, 72.46; H, 6.17; S, 10.56.

EXAMPLE 8

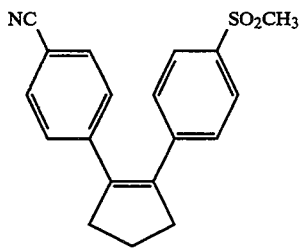

1-[2-(4-cyanophenyl)cyclopenten-1-yl]-
4-(methylsulfonyl)benzene

Step 1: Preparation of 4-Cyanophenylboronic Acid

Following the synthetic procedure outlined in Step 1 of Example 1, 4-bromobenzonitrile (Aldrich) was converted to 4-cyanophenylboronic acid: NMR (DMSO-$d_6$) d 7.76 (d, J=7 Hz, 2H), 7.91 (d, J=8 Hz, 2H).

Step 2: Preparation of 1-[2-(4-Cyanophenyl) Cyclopenten-1-yl]-4-(Methylthio)Benzene Following the synthetic procedure outlined in Step 3 of Example 1, 500 mg (1.9 mmol) of 1-(2-bromocyclopenten-1-yl)-4-(methylthio) benzene (Example 1, Step 2) was reacted with 540 mg (3.7 mmol) of 4-cyanophenylboronic acid (Step 1). Purification by silica gel chromatography (MPLC) with hexane/ethyl acetate (19:1) gave 480 mg (89%) of 1-[2-(4-cyanophenyl)cyclopenten-1-yl]-4-(methylthio)benzene as an oil: NMR (CDCl$_3$) d 2.07 (m, J=7 Hz, 2H) , 2.42 (s, 3H) , 2.89 (t, J=7 Hz, 4H) , 7.05 (d, J=8 Hz, 2H) , 7.11 (d, J=8 Hz, 2H) , 7 . 26 (d, J=8 Hz, 2H) , 7.48 (d, J=8 Hz, 2H ) .

Step 3: Preparation of 1-[2-(4-Cyanophenyl)Cyclopenten-1-yl]-4-(Methylsulfonyl) Benzene Following the synthetic procedure outlined in Step 4 of Example 1, 240 mg (0.82 mmol) of 1-[2-(4-cyanophenyl)cyclopenten-1-yl]-4-(methylthio)benzene (Step 2) was oxidized. Purification by silica gel chromatography (MPLC) with ethyl acetate/hexane (3:7) and subsequent recrystallization gave 174 mg (66%) of 1-[2-(4-cyanophenyl) cyclopenten-1-yl]-4-(methylsulfonyl)benzene as a colorless solid: mp 163.0°–164.5° C.; NMR (CDCl$_3$) d 2.13 (m, J=7 Hz, 2H), 2.95 (t, J=7 Hz, 4H), 3.05 (s, 3H), 7.22 (d, J=8 Hz, 2H), 7.30 (d, J=8 Hz, 2H), 7.51 (d, J=8 Hz, 2H), 7.79 (d, J=8 Hz, 2H); MS (EI) m/e (rel intensity) 323 (100) , 308 (4) , 244 (42); HRMS. Calc'd for $C_{19}H_{17}NO_2S$: 323.0980. Found: 323.1014. Anal. Calc'd for $C_{19}H_{17}NO_2S$: C, 70.56; H, 5.30; N, 4.33; S, 9.91. Found: C, 70.59; H, 5.34; N, 4.29; S, 9.67.

EXAMPLE 9

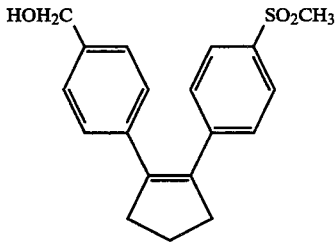

1-[2-(4-hydroxymethylphenyl)cyclopenten-
1-yl]-4-(methylsulfonyl)benzene

Step 1: Preparation of 4-Hydroxymethylphenylboronic Acid

Following the synthetic procedure outlined in Step 1 of Example 1, 4-bromobenzyl alcohol (Aldrich) was converted to 4-hydroxymethylphenyl boronic acid: NMR (DMSO-$d_6$) d 4.50 (d, J=5 Hz, 2H), 5.08 (s, 1H), 7.20–7.45 (m, 2H), 7.68–7.90 (m, 2H).

Step 2: Preparation of 1-[2-(4-Hydroxymethylphenyl)Cyclopenten-1-yl]-4-(Methylthio)Benzine Following the synthetic procedure outlined in Step 3 of Example 1, 250 mg (0.93 mmol) of 1-(2-bromocyclopenten-1-yl) -4-(methylthio) benzene (Example 1, Step 2) was reacted with 290 mg (1.9 mmol) of 4-hydroxymethylphenylboronic acid (Step 1). Purification by silica gel chromatography (MPLC) with ethyl acetate/hexane (1:4) gave 255 mg (92%) of 1-[2-(4-hydroxymethylphenyl)cyclopenten-1-yl]-4-(methylthio)benzene as a solid: mp 82°–85° C.; NMR (CDCl$_3$) d 2.04 (m, J=7 Hz, 2H) , 2.45 (s, 3H) , 2.88 (t, J=7 Hz, 4H) , 4.64 (s, 2H) , 7.08 (s, 4H) , (m, 2H) , 7.15–7.25 (m, 4H) .

Step 3: Preparation of 1-[2-(4-Hydroxymethylphenyl)Cyclopenten-1-yl]-4-(Methylsulfonyl)Benzene Following the synthetic procedure outlined in Step 4 of Example 1, 210 mg (0.71 mmol) of 1-[2-(4-hydroxymethylphenyl)cyclopenten-1-yl] -4-(methylthio)benzene (Step 2) was oxidized. Purification by silica gel chromatography with hexane/ethyl acetate (1:4) and subsequent recrystallization from ethyl acetate/hexane gave 1-[2-(4-hydroxymethyl phenyl)cyclopenten-1-yl]-4-(methylsulfonyl) benzene as a colorless solid: mp 114°–115° C.; NMR (CDCl$_{13}$) d 2.09 (m, J=7 Hz, 2H) , 2.92 (t, J=7 Hz, 4H) , 3.03 (s, 3H) , 4.67 (s, 2H) , 7.13 (d, J=8 Hz, 2H) , 7.24 (d, J=8 Hz, 1H) , 7.33(d, J=8 Hz, 2H) , 7.74 (d, J=8 Hz, 2H); MS (EI) m/e (rel intensity) 328 (100), 311 (10), 297 (21), 218 (53); HRMS. Calc'd for $C_{19}H_{20}O_3S$: 328.1133. Found: 328.1147. Anal. Calc'd for $C_{19}H_{20}O_3S$: C, 69.48; H, 6.14; S, 9.76. Found: C, 69.51; H, 6.40; S, 9.68.

EXAMPLE 10

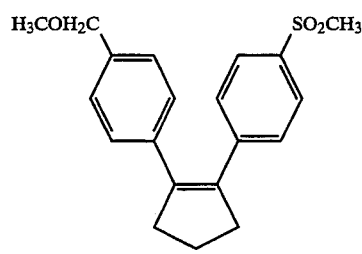

1-[2-(4-methoxymethylphenyl)cyclopenten-
1-yl]-4-(methylsulfonyl)benzene

Under nitrogen, a stirred solution of 79 mg (0.24 mmol) of 1-[2-(4-hydroxymethylphenyl)cyclopenten-1-yl]-4-(methylsulfonyl)benzene (Example 9) in 2 mL of dry THF at 0° C. was treated with 15 mg (0.6 mmol) of sodium hydride (95%); after 30 minutes, 0.1 mL (1.6 mmol) of methyl iodide was added and the reaction was allowed to warm to ambient temperature overnight. The solvent was removed in vacuo; the residue was dissolved in ethyl acetate and washed with water, dried (MgSO$_4$), and reconcentrated. Purification by silica gel chromatography (MPLC) with hexane/ethyl acetate (5:1) and subsequent lyophilization from acetonitrile/water (1:1) gave 25 mg (30%) of 1-[2-(4-methoxymethyl phenyl)cyclopenten-1-yl]-4 -(methylsulfonyl)benzene as a colorless solid: NMR (CDCl$_3$) d 2.09 (m, J=7 Hz, 2H) , 2.92 (t, J=7 Hz, 4H) , 3.03 (s, 3H) , 3.40 (s, 3H), 4.42 (s, 2H), 7.12 (d, J=8 Hz, 2H), 7.20 (d, J=8 Hz, 2H) , 7.33 (d, J=8 Hz, 2H) , 7.73 (d, J=8 Hz, 2H; MS (EI) m/e (rel intensity) 342 (100), 81 (27), 69 (62). HRMS. Calc'd for C$_{20}$H$_{22}$O$_3$S: 342.1290. Found: 342.1301. Anal. Calc'd for C$_{20}$H$_{22}$O$_3$S: C, 70.15; H, 6.48; S, 9.36. Found: C, 69.86; H, 6.64; S, 9.38.

EXAMPLE 11

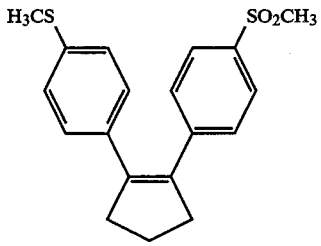

1-[2-(4-methylthiophenyl)cyclopenten-1-yl]-
4-(methylsulfonyl)benzene

Step 1: Preparation of 1-(2-Bromocyclopenten-1-yl)-4-(Methylsulfonyl)Benzene Following the synthetic procedure outlined in Step 4 of Example 1, 250 mg (0.93 mmol) of 1-(2-bromocyclopenten-1-yl)-4-(methylthio) benzene (Example 1, Step 2) was oxidized to give 280 mg (100%) of 1-(2-bromocyclopenten-1-yl)-4-(methylsulfonyl)benzene as a colorless solid: mp 103°-104° C.; NMR (CDCl$_3$) d 2.02-2.14 (m, 2H) , 2.74-2.83 (m, 2H) , 2.86-2.94 (m, 2H), 3.07 (s, 3H), 7.77 (d, J=8 Hz, 2H), 7.93 (d, J=8 Hz, 2H) .

Step 2: Preparation of 1-[2-(4-Methylthiophenyl)Cyclopenten-1-yl]-4-(Methylsulfonyl)Benzene Following a synthetic procedure which was similar to the one outlined in Step 3 of Example 1, 270 mg (0.9 mmol) of 1-(2-bromocyclopenten-1-yl)-4-(methylsulfonyl)benzene (Step 1) was reacted with 300 mg (1.8 mmol) of 4-methylthiophenylboronic acid (Example 1, Step 1). Purification by silica gel chromatography (MPLC) with hexane/ethyl acetate (4:1) gave 265 mg (86%) of 1-[2-(4-methylthiophenyl)cyclopenten-1-yl]-4-(methylsulfonyl)benzene as a colorless solid: mp 138°-139° C.; NMR (CDCl$_3$) d 2.08 (m, J=7 Hz, 2H), 2.47 (s, 3H), 2.90 (t, J=7 Hz, 4H), 3.04 (s, 3H), 7.06 (d, J=8 Hz, 2H), 7.11 (d, J=8 Hz, 2H), 7.34 (d, J=8 Hz, 2H), 7.75 (d, J=8 Hz, 2H); MS (EI) m/e (rel intensity) 344 (100), 297 (4), 218 (33); HRMS. Calc'd for C$_{19}$H$_{20}$O$_2$S$_2$: 344.0905. Found: 344.0907. Anal. Calc'd for C$_{19}$H$_{20}$O$_2$S$_2$: C, 66.24; H, 5.85; S, 18.16. Found: C, 66.28; H, 5.81; S, 18.95.

EXAMPLE 12

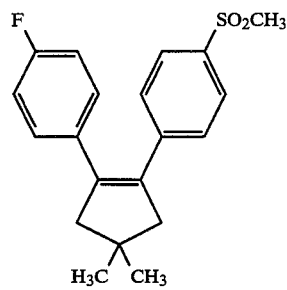

1-[2-(4-fluorophenyl)-4,4-dimethylcyclopenten-
1-yl]-4-(methylsulfonyl)benzene

Step 1: Preparation of the Ethyl Acetal of Mucobromic Acid

Under nitrogen, a stirred solution of 500 g (1.94 mmol) of mucobromic acid (Lancaster) and 2 g of p-toluenesulfonic acid monohydrate in 600 mL of toluene and 400 mL of absolute ethanol was heated to reflux for 6 h during which time 150 mL of a water, toluene, and ethanol azeotrope was removed by distillation. The solution was concentrated in vacuo; the residue was dissolved in 1500 mL of ethyl acetate and washed with water, saturated sodium carbonate, and brine, dried (Na$_2$SO$_4$), and reconcentrated to give 440 g (79%) of the ethyl acetal of mucobromic acid (5 in Synthetic Scheme II) as an oil: NMR (CDCl$_3$) d 1.31 (t, J=7 Hz, 3H), 3.73-3.96 (m, 2H), 5.81 (s, 1H).

Step 2: Preparation of Cis-2,3-Dibromobut-2-ene-1,4-Diol

Under nitrogen, a stirred solution of 150 g (525 mmol) of the ethyl acetal of mucobromic acid (Step 1) in 150 mL of anhydrous THF at −78 ° C. was treated with 1400 mL of diisobutylaluminum hydride (1.5 M in toluene) over a 30 minute period. The solution was allowed to warm to ambient temperature and stirred for 2 h. The reaction was slowly treated (maintaining the temperature below 10° C.) with 100 mL of acetone followed by 50 mL of 2.5 N sodium hydroxide. Water (1000 mL) was added and the solution extracted 5 times with ethyl acetate. The combined extracts were washed with brine, dried (Na$_2$SO$_4$), and concentrated. The residue was washed 3 times with hexane and dried in vacuo to give 88.5 g (69%) of cis-2,3-dibromo-2-ene-1,4-diol (6 in Synthetic Scheme II) as a colorless solid: mp 66°-67° C.; NMR (DMSO-d$_6$) d 4.27 (d, J=6 Hz, 4H), 5.44 (t, J=6 Hz, 2H ) .

Step 3: Preparation of Cis-1,2,3,4-Tetrabromobut-2-ene

Under nitrogen, a stirred solution of 25.2 g (102 mmol) of cis-2,3-dibromobut-2-ene-1,4-diol (Step 2) in 150 mL of methylene chloride at 0° C. was treated with 9.6 mL of phosphorus tribromide. The solution was allowed to warm to ambient temperature where it was allowed to stir for 1 h prior to the addition of ice water. The aqueous phase was extracted 5 times with methylene chloride; these extracts were combined with the original methylene chloride phase and washed with water, saturated sodium carbonate, brine, dried (Na$_2$SO$_4$), and concentrated in vacuo to give 18 g (47%) of cis-1,2,3,4-tetrabromobut-2-ene [7 (X=Br) in Synthetic Scheme II] as an oil: NMR (CDCl$_3$) d 4.40 (s, 4H) .

Step 4: Preparation of 1,2-Dibromo-4,4-Di(Carboethoxy)Cyclopentene

Under nitrogen, a solution of 9.7 g (60.6 mmol) of diethyl malonate in anhydrous THF at −10° C. was treated with 2.9 g (121 mmol) of sodium hydride (95%) and allowed to stir for 30 min. The resulting solution was then added slowly to 15 g (40.4 mmol) of cis-1,2,3,4-tetrabromobut-2-ene (Step 3) in 350 mL of anhydrous THF at −78° C. The reaction was allowed to warm to ambient temperature overnight prior to concentration in vacuo. The residue was dissolved in ethyl acetate and washed with water, dried ($Na_2SO_4$), and reconcentrated. Purification by silica gel chromatography (Waters Prep-500) with ethyl acetate/hexane (1:99) gave 3.7 g (25%) of 1,2,-dibromo-4,4-di(carboethoxy)-cyclopentene (8 in Synthetic Scheme II) as a colorless oil: NMR ($CDCl_3$) d 1.26 (t, J=7 Hz, 6H), 3.26 (s, 4H), 4.22 (m, J=7 Hz, 4H); MS (FAB) for M+H m/e: 373, 371, 369.

Step 5: Preparation of 1,2-Dibromo-4,4-Di(Hydroxymethyl)Cyclopentene

Under nitrogen, a stirred solution of 8.7 g (23.5 mmol) of 1,2-dibromo-4,4-di(carboethoxy)cyclopentene (Step 4) in 70 mL of anhydrous THF at −78° C. was treated with 80 mL of diisobutylaluminum hydride (1.5 M in toluene) over a 20 minute period. The reaction was allowed to warm to ambient temperature overnight and was slowly treated with 20 mL of acetone followed by 10 mL of 2.5 N sodium hydroxide. Water (100 mL) was added and the solution extracted 5 times with ethyl acetate. The combined extracts were washed with brine, dried ($Na_2SO_4$), and concentrated in vacuo to give 5.7 g (85%) of 1,2-dibromo-4,4-di(hydroxymethyl)cyclopentene (10 in Synthetic Scheme III) as a colorless oil: NMR ($CDCl_3$) d 2.20 (s, 2H), 2.50 (s, 4H), 3.70 (s, 4H).

Step 6: Preparation of 1,2-Dibromo-4,4-Di(Tosylmethyl)Cyclopentene

Under nitrogen, a stirred solution of 5.7 g (19.9 mmol) of 1,2-dibromo-4,4-di(hydroxymethyl)cyclopentene (Step 5) in 50 mL of pyridine at ambient temperature was treated with 19 g (99.7 mmol) of p-toluenesulfonyl chloride. The reaction was allowed to stir overnight and was concentrated in vacuo. The residue was dissolved ethyl acetate and washed twice with 3% hydrochloric acid followed by brine. The solution was dried ($Na_2SO_4$) and concentrated in vacuo to give 5.2 g (44%) of 1,2-dibromo-4,4-di(tosylmethyl)cyclopentene (14 in Synthetic Scheme V) as a colorless semisolid: NMR ($CDCl_3$) d 2.42 (s, 4H), 2.47 (s, 6H), 3.90 (s, 4H), 7.37 (d, J=8 Hz, 4H), 7.74 (d, J=8 Hz, 4H).

Step 7: Preparation of 1,2-Dibromo-4,4-Di(Iodomethyl)Cyclopentene

Under nitrogen, a stirred solution of 5.2 g (8.7 mmol) of 1,2-dibromo-4,4-di(tosylmethyl)cyclopentene (Step 6) and 13 g (86 mmol) of sodium iodide in 40 mL of $DMF/H_2O$ (3:1) was heated to 150° C. in an oil bath overnight. The reaction was cooled, diluted with 200 mL of ethyl acetate, and washed with water. Drying ($Na_2SO_4$) and concentrating in vacuo gave 3.7 g (84%) of 1,2-dibromo-4,4-di(iodomethyl)cyclopentene (15 in Synthetic Scheme V) as an oil: NMR ($CDCl_3$) d 2.70 (s, 4H), 3.50 (s, 4H).

Step 8: Preparation of 1,2-Dibromo-4,4-Dimethylcyclopentene

Under nitrogen, a stirred solution of 3.7 g (7.3 mmol) of 1,2-dibromo-4,4-di(iodomethyl)cyclopentene (Step 7) and 1.3 g (20.6 mmol) of sodium cyanoborohydride in 15 mL of hexamethylphosphoramide (HMPA) was heated to 100° C. in an oil bath overnight. The reaction was cooled, diluted with 50 mL of water, and extracted 5 times with ethyl acetate/hexane (1:5). The combined extracts were washed 3 times with water, dried ($Na_2SO_4$), and concentrated in vacuo. Purification by silica gel chromatography (Waters Prep-500) with hexane gave 1.3 g (70%) of 1,2-dibromo-4,4-dimethylcyclopentene (16 in Synthetic Scheme V) as a colorless oil: NMR ($CDCl_3$) d 1.16 (s, 6H), 2.44 (s, 4H); MS (EI) m/e (rel intensity) 256 (24), 254 (63), 252 (44), 175 (26), 173 (29), 94 (100).

Step 9: Preparation of 1-[2-(4-Fluorophenyl)-4,4-Dimethylcyclopenten-1yl]-4-(Methylthio)Benzene Under nitrogen, 1.3 g (5.1 mmol) of 1,2-dibromo-4,4-dimethylcyclopentene (Step 8) was reacted with 600 mg (4.3 mmol) of 4-fluorophenylboronic acid (Lancaster) in 23 mL of toluene, 15 mL of ethanol, and 10 mL of 2M $Na_2CO_3$ in the presence of 250 mg (5 mol %) of $Pd(PPh_3)_4$. The reaction was vigorously stirred at reflux overnight and concentrated in vacuo. The residue was dissolved in ethyl acetate and washed with water, dried ($Na_2SO_4$), and reconcentrated. Purification by silica gel chromatography (MPLC) with hexane gave 250 mg of 1-(2-bromocyclopenten-1-yl)-4-fluorobenzene (38 in Synthetic Scheme X when $R^1$ and $R^2$=$CH_3$, $R^5$=F, $R^3$, $R^4$, $R^6$, and $R^7$=H) as a pale yellow oil which was reacted with 200 mg (1.2 mmol) of 4-methylthiophenylboronic acid (Example 1, Step 1) in 5.2 mL of toluene, 3.4 mL of ethanol, and 2.2 mL of 2M $Na_2CO_3$ in the presence of 40 mg (5 mol %) of $Pd(PPh_3)_4$. The reaction was vigorously stirred at reflux for 6 h and concentrated in vacuo. The residue was dissolved in ethyl acetate and washed with water, dried ($Na_2SO_4$), and reconcentrated. Purification by silica gel chromatography (MPLC) with hexane gave 120 mg of 1-[2-(4-fluorophenyl)-4,4-dimethyl cyclopenten-1-]-4-(methylthio)benzene (41 in Synthetic Scheme X when $R^1$ and $R^2$=$CH_3$, $R^5$=F, $R^{10}$=$SCH_3$, $R^3$, $R^4$, $R^6$, $R^7$, $R^8$, $R^9$, $R^{11}$, and $R^{12}$=H) as an oil: NMR ($CDCl_3$) d 1.20 (s, 6H00, 2.42 (s, 3H), 2.63 (s, 4H), 6.90 (t, J=8 Hz, 2H), 7.00–7.18 (m, 4H), 7.30–7.60 (m, 2H).

Step 10: Preparation of 1-[2-(4-Fluorophenyl)-4,4-Dimethylcyclopenten-1-yl]-4-(Methylsulfonyl)Benzene A solution of 120 mg (0.39 mmol) of 1-[2-(4-fluorophenyl)-4,4-dimethylcyclopenten-1-yl]-4-(methylthio)benzene (Step 9) in 3 mL of methanol/water (1:1) was slowly treated with 470 mg (0.76 mmol) of Oxone® [2 $KHSO_5.KHSO_4.K_2SO_4$] in 2 mL of water. After stirring for 4 h, the solvent was removed in vacuo. The residue was dissolved in ethyl acetate and washed with water and brine, dried ($MgSO_4$), and reconcentrated. Purification by silica gel chromatography (MPLC) with hexane/ethyl acetate (5:1) and subsequent lyophilization from acetonitrile/water (1:1) gave 50 mg (38%) of 1-[2-(4-fluorophenyl)-4,4-dimethyl cyclopenten-1-yl]-4-(methylsulfonyl)benzene (41 in Synthetic Scheme X when $R^1$ and $R^2$=$CH_3$, $R^5$=F, $R^{10}$=$SO_2CH_3$, $R^3$, $R^4$, $R^6$, $R^7$, $R^8$, $R^9$, $R^{11}$, and $R^{12}$=H) as a colorless solid: NMR (CDCl$_3$) d 1.24 (s, 6H), 2.71 (s, 4H), 3.4 (s, 3H), 6.92 (t, J=8 Hz, 2H), 7.05–7.12 (m, 2H), 7.30 (d, J=9 Hz, 2H), 7.75 (d, J=9 Hz, 3H); MS (EI) m/e (rel intensity) 344 (100), 329 (33), 250 (18), 235 (20), 109 (35), 69 (44); HRMS. Calc'd for C$_{20}$H$_{21}$FO$_2$S: 344.1246. Found: 344.1272.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol., Med.,* 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.25% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterhess and Bliven, *Laboratory Models for Testing NSAIDS*, in *Nonsteroidal Anti-Inflammatory Drugs*, (J. Lombardino, ed. 1985)). Results are shown in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 20 mg/kg body weight |
|---|---|---|
| 1 | 33 | 66 |
| 2 | 39 | |
| 3 | 33 | 41 |
| 4 | 25 | |
| 5 | 16 | |
| 6 | 39 | 29 |
| 11 | 28 | 39 |
| 12 | *45 | |

*Assay performed at 20 mg/kg body weight.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 1000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula II

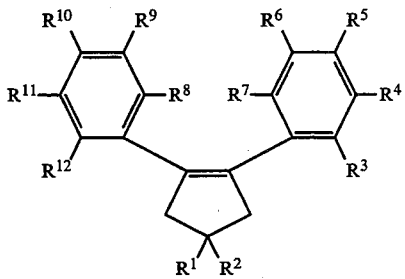

wherein each of $R^1$ and $R^2$ is independently selected from alkyl, hydrido, hydroxyalkyl, halo, haloalkyl, alkylcarboxyl and carboxyl; wherein $R^5$ is alkylsulfonyl or sulfamyl; and wherein each of $R^3$, $R^4$, and $R^6$ through $R^{12}$ is independently selected from hydrido, halo, alkyl, alkylthio, cyano, haloalkyl, alkoxy, hydroxyalkyl, alkoxyalkyl, alkylsulfonyl and sulfamyl;

or a pharmaceutically suitable salt thereof.

2. Compound of claim 1 wherein $R^1$ and $R^2$ are identical radicals selected from hydrido, alkyl, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein each of $R^3$, $R^4$, $R^6$ through $R^9$, $R^{11}$ and $R^{12}$ is independently selected from hydrido, alkyl and halo; wherein $R^5$ is alkylsulfonyl or sulfamyl; and wherein $R^{10}$ is selected from hydrido, halo, alkyl, alkylthio, cyano, haloalkyl, alkoxy, hydroxyalkyl and alkoxyalkyl; or a pharmaceutically-acceptable salt thereof.

3. The compound of claim 2 wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; wherein $R^5$ is methylsulfonyl or sulfamyl; and wherein $R^{10}$ is selected from hydrido, fluoro, chloro, bromo, iodo, methyl, ethyl, methoxy, methylthio, cyano, trifluoromethyl, hydroxymethyl and methoxymethyl; or a pharmaceutically-acceptable salt thereof.

4. Compound of claim 3 selected from compounds, and their pharmaceutically-acceptable salts, of the group consisting of 1-(2-phenylcyclopenten-1-yl)-4-(methylsulfonyl)benzene, 1-[2-(4-fluorophenyl)cyclopenten-1-yl]-4-(methylsulfonyl)benzene;

1-[2-(4-chlorophenyl)cyclopenten-1-yl]-4-(methylsulfonyl)benzene;

1-[2-(4-methylphenyl)cyclopenten-1-yl)-4-methylsulfonyl)benzene;

1-[2-(4-methylthiophenyl)cyclopenten-1-yl)-4-(methylsulfonyl)benzene;

1-[2-(4-cyanophenyl)cyclopenten-1-yl)-4-(methylsulfonyl)benzene;

1-[2-(4-trifluoromethylphenyl)cyclopenten-1-yl)-4-(methylsulfonyl)benzene;

1-[2-(4-hydroxymethylphenyl)cyclopenten-1-yl)-4-(methylsulfonyl)benzene;

1-[2-(4-methoxymethylphenyl)cyclopenten-1-yl)-4-(methylsulfonyl)benzene;

1-[2-(4-fluoro-2-methylphenyl)cyclopenten-1-yl)-4-(methylsulfonyl)benzene;

1-[2-(2,4-dimethylphenyl)cyclopenten-1-yl]-4-(methylsulfonyl)benzene;

1-[2-(2,4-difluorophenyl)cyclopenten-1-yl]-4-(methylsulfonyl)benzene;

1-[2-(2,4-dichlorophenyl)cyclopenten-1-yl]-4-(methylsulfonyl)benzene;

4-[2-(4-fluorophenyl)cyclopenten-1-yl]benzenesulfonamide;

4-[2-(4-chlorophenyl)cyclopenten-1-yl]benzenesulfonamide;

4-[2-(4-methylphenyl)cyclopenten-1-yl]benzenesulfonamide;

4-[2-(4-trifluoromethylphenyl)cyclopenten-1-yl]benzenesulfonamide;

4-[2-(2,4-dimethylphenyl)cyclopenten-1-yl]benzenesulfonamide;

4-[2-(2,4-difluorophenyl)cyclopenten-1-yl]benzenesulfonamide;

4-[2-(2,4-dichlorophenyl)cyclopenten-1-yl]benzenesulfonamide;

1-[2-(4-fluorophenyl)-4,4-dimethylcyclopenten-1-yl]-4-(methylsulfonyl)benzene;

1-[2-(4-fluorophenyl)-4,4-difluorocyclopenten-1-yl]-4-(methylsulfonyl)benzene;

1-[2-(4-trifluoromethylphenyl)-4,4-dimethylcyclopenten-1-yl]-4-(methylsulfonyl)benzene;

1-[2-(4-trifluoromethylphenyl)-4,4-difluorocyclopenten-1-yl]-4-(methylsulfonyl)benzene;

4-[2-(4-fluorophenyl)-4,4-dimethylcyclopenten-1-yl]benzenesulfonamide;

4-[2-(4-fluorophenyl)-4,4-difluorocyclopenten-1-yl]benzenesulfonamide;

4-[2-(4-trifluoromethylphenyl)-4,4-dimethylcyclopenten-1-yl]benzenesulfonamide;

4-[2-(4-trifluoromethylphenyl)-4,4-difluorocyclopenten-1-yl]benzenesulfonamide;

1-[2-(4-fluorophenyl)-4-carboxycyclopenten-1-yl]-4(methylsulfonyl)benzene;

1-[2-(4-trifluoromethylphenyl)-4-carboxycyclopenten-1-yl]-4-(methylsulfonyl)benzene;

4-[2-(4-fluorophenyl)-4-carboxycyclopenten-1-yl]benzenesulfonamide; and

4-[2-(4-trifluoromethylphenyl)-4-carboxycyclopenten-1-yl]benzenesulfonamide.

5. Compound of claim 3 which is 1-[2-(4-fluorophenyl)cyclopenten-1-yl]-4-(methylsulfonyl)benzene, or a pharmaceutically-acceptable salt thereof.

6. Compound of claim 3 which is 1-[2-(4-fluorophenyl)-4,4-dimethylcyclopenten-1-yl]-4-(methylsulfonyl)benzene, or a pharmaceutically-acceptable salt thereof.

7. Compound of claim 3 which is 4-[2-(4-fluorophenyl)cyclopenten-1-yl)benzenesulfonamide, or pharmaceutically-acceptable salt thereof.

8. Compound of claim 3 which is 4-[2-(4-fluorophenyl)-4,4-dimethylcyclopenten-1-yl)benzenesulfonamide, or a pharmaceutically-acceptable salt thereof.

9. A compound of Formula III

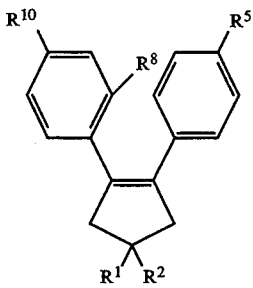

III wherein each of $R^1$ and $R^2$ is independently selected from alkyl, hydrido, hydroxyalkyl, halo, haloalkyl, alkylcarboxyl and carboxyl;
wherein $R^5$ is alkylsulfonyl or sulfamyl;
wherein $R^8$ is selected from hydrido, alkyl and halo; and wherein $R^{10}$ is selected from hydrido, malo, alkyl, alkylthio, cyano, haloalkyl, alkoxy, hydroxyalkyl and alkoxyalkyl; or a pharmaceutically-acceptable salt thereof.

10. The compound of claim 9 wherein $R^1$ and $R^2$ are identical radicals selected from hydrido and methyl; wherein $R^5$ is methylsulfonyl or sulfamyl; wherein $R^8$ is selected from hydrido, methyl and chloro; and wherein $R^{10}$ is selected from hydrido, fluoro, chloro, methyl, methylthio, cyano, trifluoromethyl, hydroxymethyl and methoxymethyl; or a pharmaceutically-acceptable salt thereof.

11. A pharmaceutical composition comprising a therapeutically-effective amount of an anti-inflammatory compound and a pharmaceutically-acceptable carrier or diluent, said compound selected from compounds of Formula II

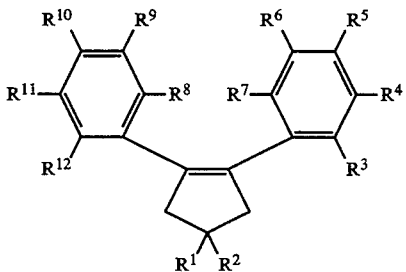

II wherein each of $R^1$ and $R^2$ is independently selected from alkyl, hydrido, hydroxyalkyl, halo, haloalkyl, alkylcarboxyl and carboxyl; wherein $R^5$ is alkylsulfonyl or sulfamyl; and
wherein each of $R^3$, $R^4$ and $R^6$ through $R^{12}$ is independently selected from hydrido, halo, alkyl, alkylthio, cyano, haloalkyl, alkoxy, hydroxyalkyl, alkoxyalkyl, alkylsulfonyl and sulfamyl; or a pharmaceutically suitable salt thereof.

12. The composition of claim 11 wherein $R^1$ and $R^2$ are identical radicals selected from hydrido alkyl, hydroxyalkyl, halo, haloalkyl, alkylcarboxyl and carboxyl; or wherein further $R^1$ is hydrido and $R^2$ is selected from alkyl, hydroxyalkyl, halo, haloalkyl, alkylcarboxyl and carboxyl; wherein each of $R^3$, $R^4$, $R^6$ through $R^9$, $R^{11}$ and $R^{12}$ is independently selected from hydrido, alkyl and halo; wherein $R^5$ is alkylsulfonyl or sulfamyl; and wherein $R^{10}$ is selected from hydrido, halo, alkyl, alkylthio, cyano, haloalkyl, alkoxy, hydroxyalkyl and alkoxyalkyl; or a pharmaceutically-acceptable salt thereof.

13. The composition of claim 12 wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; wherein $R^5$ is methylsulfonyl or sulfamyl; and wherein $R^{10}$ is selected from hydrido, fluoro, chloro, bromo, iodo, methyl, ethyl, methoxy, methylthio, cyano, trifluoromethyl, hydroxymethyl and methoxymethyl; or a pharmaceutically-acceptable salt thereof.

14. The composition of claim 13 wherein said anti-inflammatory compound is selected from compounds, and their pharmaceutically-acceptable salts, of the group consisting of
1-[2-(4-phenyl)cyclopenten-1-yl]-4-(methylsulfonyl)benzene,
1-[2-(4-fluorophenyl)cyclopenten-1-yl]-4-(methylsulfonyl)benzene;
1-[2-(4-chlorophenyl)cyclopenten-1-yl]-4-(methylsulfonyl)benzene;
1-[2-(4-methylphenyl)cyclopenten-1-yl)-4-methylsulfonyl)benzene;
1-[2-(4-methylthiophenyl)cyclopenten-1-yl)-4-(methylsulfonyl)benzene;
1-[2-(4-cyanophenyl)cyclopenten-1-yl ) -4-(methylsulfonyl)benzene;
1-[2-(4-trifluoromethylphenyl)cyclopenten-1-yl)-4-(methylsulfonyl)benzene;
1-[2-(4-hydroxymethylphenyl)cyclopenten-1-yl)-4-(methylsulfonyl)benzene;
1-[2-(4-methoxymethylphenyl)cyclopenten-1-yl)-(methylsulfonyl)benzene;
1-[2-(4-fluoro-2-methylphenyl)cyclopenten-1-yl)-4-(methylsulfonyl)benzene;
1-[2-(2,4-dimethylphenyl)cyclopenten-1-yl]-4-(methylsulfonyl)benzene;
1-[2-(2,4-difluorophenyl)cyclopenten-1-yl]-4-(methylsulfonyl)benzene;
1-[2-(2,4-dichlorophenyl)cyclopenten-1-yl]-4-(methylsulfonyl)benzene;
4-[2-(4-fluorophenyl)cyclopenten-1-yl]benzenesulfonamide;
4-[2-(4-chlorophenyl)cyclopenten-1-yl]benzenesulfonamide;
4-[2-(4-methylphenyl)cyclopenten-1-yl]benzenesulfonamide;
4-[2-(4-trifluoromethylphenyl)cyclopenten-1-yl]benzenesulfonamide;
4-[2-(2,4-dimethylphenyl)cyclopenten-1-yl]benzenesulfonamide;
4-[2-(2,4-difluorophenyl)cyclopenten-1-yl]benzenesulfonamide;
4-[2-(2,4-dichlorophenyl)cyclopenten-1-yl]benzenesulfonamide;
1-[2-(4-fluorophenyl)-4,4-dimethylcyclopenten-1-yl]-4-(methylsulfonyl)benzene;
1-[2-(4-fluorophenyl)-4,4-difluorocyclopenten-1-yl]-4-(methylsulfonyl)benzene;
1-[2-(4-trifluoromethylphenyl)-4,4-dimethylcyclopenten-1-yl]-4-(methylsulfonyl)benzene;
1-[2-(4-trifluoromethylphenyl) -4,4-difluorocyclopenten-1-yl]-4-(methylsulfonyl)benzene;
4-[2-(4-fluorophenyl)-4,4-dimethylcyclopenten-1-yl]benzenesulfonamide;

4-[2-(4-fluorophenyl)-4,4-difluorocyclopenten-1-yl]benzenesulfonamide;

4-[2-(4-trifluoromethylphenyl)-4,4-dimethylcyclopenten-1-yl]benzenesulfonamide;

4-[2-(4-trifluoromethylphenyl)-4,4-difluorocyclopenten-1-yl]benzenesulfonamide;

1-[2-(4-fluorophenyl)-4-carboxycyclopenten-1-yl]-4-(methylsulfonyl)benzene;

1-[2-(4-trifluoromethylphenyl)-4-carboxycyclopenten-1-yl]-4-(methylsulfonyl)benzene;

4-[2-(4-fluorophenyl)-4-carboxycyclopenten-1-yl]benzenesulfonamide; and

4-[2-(4-trifluoromethylphenyl)-4-carboxycyclopenten-1-yl]benzenesulfonamide.

15. The composition of claim 13 wherein said anti-inflammatory compound is 1-[2-(4-fluorophenyl)cyclopenten-1-yl]-4-(methylsulfonyl)benzene, or a pharmaceutically-acceptable salt thereof.

16. The composition of claim 13 wherein said anti-inflammatory compound is 1-[2-(4-fluorophenyl)-4,4-dimethylcyclopenten-1-yl]-4-(methylsulfonyl)benzene, or a pharmaceutically-acceptable salt thereof.

17. The composition of claim 13 wherein said anti-inflammatory compound is 4-[2-(4-fluorophenyl)cyclopenten-1-yl]benzenesulfonamide, or a pharmaceutically-acceptable salt thereof.

18. The composition of claim 13 wherein said anti-inflammatory compound is 4-[2-(4-fluorophenyl)-4,4-dimethylcyclopenten-1-yl]benzenesulfonamide.

19. A method of treating inflammation or an inflammation-associated disorder, said method comprising administering to a subject having said inflammation or said inflammation-associated disorder, a therapeutically-effective amount of a compound of Formula II

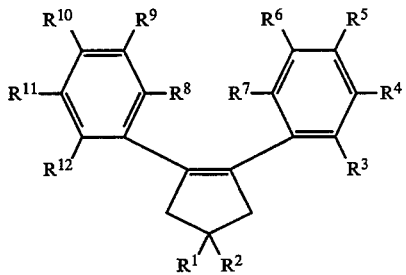

wherein each of $R^1$ and $R^2$ is independently selected from alkyl, hydrido, hydroxyalkyl, halo, haloalkyl, alkylcarboxyl and carboxyl; wherein $R^5$ is alkylsulfonyl or sulfamyl; and wherein each of $R^3$, $R^4$ and $R^6$ through $R^{12}$ is independently selected from hydrido, halo, alkyl, alkylthio, cyano, haloalkyl, alkoxy, hydroxyalkyl, alkoxyalkyl, alkylsulfonyl and sulfamyl; or a pharmaceutically suitable salt thereof.

20. The method of claim 19 wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, alkyl and halo; wherein $R^5$ is alkylsulfonyl or sulfamyl; and wherein $R^{10}$ is selected from hydrido, halo, alkyl, alkylthio, cyano, haloalkyl, alkoxy, hydroxyalkyl and alkoxyalkyl; or a pharmaceutically-acceptable salt thereof.

21. The method of claim 20 wherein $R^1$ and $R^2$ are identical radicals selected from hydrido, methyl, ethyl, fluoro, hydroxymethyl, carbomethoxy, trifluoromethyl, carboxyl and fluoromethyl; or wherein further $R^1$ is hydrido and $R^2$ is selected from methyl, ethyl, fluoro, hydroxymethyl, carbomethoxy, trifluoromethyl, carboxyl and fluoromethyl; wherein each of $R^3$, $R^4$, $R^6$ through $R^9$, $R^{11}$ and $R^{12}$ is independently selected from hydrido, methyl, fluoro and chloro; wherein $R^5$ is methylsulfonyl or sulfamyl; and wherein $R^{10}$ is selected from hydrido, fluoro, chloro, bromo, iodo, methyl, ethyl, methoxy, methylthio, cyano, trifluoromethyl, hydroxymethyl and methoxymethyl; or a pharmaceutically-acceptable salt thereof.

22. The method of claim 21 wherein said compound is selected from compounds, and their pharmaceutically-acceptable salts, of the group consisting of 1-[2-(4-phenyl)cyclopenten-1-yl]-4-(methylsulfonyl)benzene, 1-[2-(4-fluorophenyl)cyclopenten-1-yl]-4-(methylsulfonyl)benzene;

1-[2-(4-chlorophenyl)cyclopenten-1-yl]-4-(methylsulfonyl)benzene;

1-[2-(4-methylphenyl)cyclopenten-1-yl)-4-methylsulfonyl)benzene;

1-[2-(4-methylthiophenyl)cyclopenten-1-yl)-4-(methylsulfonyl)benzene;

1-[2-(4-cyanophenyl)cyclopenten-1-yl)-4-(methylsulfonyl)benzene;

1-[2-(4-trifluoromethylphenyl)cyclopenten-1-yl)-4-(methylsulfonyl)benzene;

1-[2-(4-hydroxymethylphenyl)cyclopenten-1-yl)-4-(methylsulfonyl)benzene;

1-[2-(4-methoxymethylphenyl)cyclopenten-1-yl)-4-(methylsulfonyl)benzene;

1-[2-(4-fluoro-2-methylphenyl)cyclopenten-1-yl)-4-(methylsulfonyl)benzene;

1-[2-(2,4-dimethylphenyl)cyclopenten-1-yl]-4-(methylsulfonyl)benzene;

1-[2-(2,4-difluorophenyl)cyclopenten-1-yl]-4-(methylsulfonyl)benzene;

1-[2-(2,4-dichlorophenyl)cyclopenten-1-yl]-4-(methylsulfonyl)benzene;

4-[2-(4-fluorophenyl)cyclopenten-1-yl]benzenesulfonamide;

4-[2-(4-chlorophenyl)cyclopenten-1-yl]benzenesulfonamide;

4-[2-(4-methylphenyl)cyclopenten-1-yl]benzenesulfonamide;

4-[2-(4-trifluoromethylphenyl)cyclopenten-1-yl]benzenesulfonamide;

4-[2-(2,4-dimethylphenyl)cyclopenten-1-yl]benzenesulfonamide;

4-[2-(2,4-difluorophenyl)cyclopenten-1-yl]benzenesulfonamide;

4-[2-(2,4-dichlorophenyl)cyclopenten-1-yl]benzenesulfonamide;

1-[2-(4-fluorophenyl)-4,4-dimethylcyclopenten-1-yl]-4-(methylsulfonyl)benzene;

1-[2-(4-fluorophenyl)-4,4-difluorocyclopenten-1-yl]-4-(methylsulfonyl)benzene;

1-[2-(4-trifluoromethylphenyl)-4,4-dimethylcyclopenten-1-yl]-4-(methylsulfonyl)benzene;

1-[2-(4-trifluoromethylphenyl)-4,4-difluorocyclopenten-1-yl]-4-(methylsulfonyl)benzene;

4-[2-(4-fluorophenyl)-4,4-dimethylcyclopenten-1-yl]benzenesulfonamide;

4-[2-(4-fluorophenyl)-4,4-difluorocyclopenten-1-yl]benzenesulfonamide;

4-[2-(4-trifluoromethylphenyl)-4,4-dimethylcyclopenten-1-yl]benzenesulfonamide;

4-[2-(4-trifluoromethylphenyl)-4,4-difluorocyclopenten-1-yl]benzenesulfonamide;

1-[2-(4-fluorophenyl)-4-carboxycyclopenten-1-yl]-4-(methylsulfonyl)benzene;

1-[2-(4-trifluoromethylphenyl)-4-carboxycyclopenten-1-yl]-4-(methylsulfonyl)benzene;

4-[2-(4-fluorophenyl)-4-carboxycyclopenten-1-yl]benzenesulfonamide; and

4-[2-(4-trifluoromethylphenyl)-4-carboxycyclopenten-1-yl]benzenesulfonamide.

23. The method of claim 21 where the compound is 1-[2-(4-fluorophenyl)cyclopenten-1-yl]-4(methylsulfonyl) benzene, or a pharmaceutically-acceptable salt thereof.

24. The method of claim 21 where the compound is 1-[2-(4-fluorophenyl)-4,4-dimethylcyclopenten-1-yl]-4-(methylsulfonyl)benzene, or a pharmaceutically-acceptable salt thereof.

25. The method of claim 21 where the compound is 4-[2-(4-fluorophenyl)cyclopenten-1-yl]benzenesulfonamide, or a pharmaceutically-acceptable salt thereof.

26. The method of claim 21 where the compound is 4-[2-(4-fluorophenyl)-4,4-dimethylcyclopenten-1-yl]-4-benzenesulfonamide, or a pharmaceutically acceptable salt thereof.

27. The method of claim 19 for use in treatment of inflammation.

28. The method of claim 19 for use in treatment of an inflammation-associated disorder.

29. The method of claim 28 the inflammation-associated disorder is arthritis.

30. The method of claim 28 wherein the inflammation-associated disorder is pain.

31. The method of claim 28 wherein the inflammation-associated disorder is fever.

* * * * *